United States Patent
Ginsburg et al.

(10) Patent No.: US 7,494,504 B2
(45) Date of Patent: *Feb. 24, 2009

(54) METHODS AND APPARATUS FOR REGIONAL AND WHOLE BODY TEMPERATURE MODIFICATION

(75) Inventors: Robert Ginsburg, Greenwood Village, CO (US); Arlene S. Ginsburg, legal representative, Greenwood Village, CO (US); Timothy R. Machold, Moss Beach, CA (US); Michael T. Dineen, Palo Alto, CA (US)

(73) Assignee: Zoll Circulation, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/724,075

(22) Filed: Mar. 13, 2007

(65) Prior Publication Data

US 2007/0233212 A1    Oct. 4, 2007

Related U.S. Application Data

(63) Continuation of application No. 10/626,007, filed on Jul. 24, 2003, now Pat. No. 7,217,282, which is a continuation of application No. 09/138,830, filed on Aug. 24, 1998, now Pat. No. 6,620,188, which is a continuation-in-part of application No. 08/584,013, filed on Jan. 8, 1996, now Pat. No. 5,837,003, which is a continuation-in-part of application No. 08/324,853, filed on Oct. 18, 1994, now Pat. No. 5,486,208, which is a continuation of application No. 08/015,714, filed on Feb. 10, 1993, now abandoned.

(51) Int. Cl.
*A61F 7/00* (2006.01)
*A61F 7/12* (2006.01)

(52) U.S. Cl. .......................................... 607/113; 607/96

(58) Field of Classification Search ....................... None
See application file for complete search history.

(56) References Cited

U.S. PATENT DOCUMENTS 2,308,484 A    1/1943 Auzin et al.
(Continued)

FOREIGN PATENT DOCUMENTS

DE    4100290    7/1991
(Continued)

OTHER PUBLICATIONS

A Technique for The Production of Hypothermia; Prelim. Report Charles B. Ripstein, M.D., et al.; Dept. of Surgery, Maimonides Hospital and State Univ. of NY, College of Medicine at N.Y.; Apr. 7, 1953.
(Continued)

*Primary Examiner*—Robert L Nasser
(74) *Attorney, Agent, or Firm*—Robert D. Buyan; Stout, Uxa, Buyan & Mullins, LLP

(57) ABSTRACT

Methods and apparatus for temperature modification of selected body regions including an induced state of local hypothermia of the brain region for neuroprotection. A heat exchange catheter is provided with heat transfer fins projecting or extending outward from the catheter which may be inserted into selected blood vessels or body regions to transfer heat with blood or fluid in the selected blood vessels or body regions. Another aspect of the invention further provides methods and apparatus for controlling the internal body temperature of a patient. By selectively heating or cooling a portion of the catheter lying within a blood vessel, heat may be transferred to or from blood flowing within the vessel to increase or decrease whole body temperature or the temperature of a target region. Feed back from temperature sensors located within the patient's body allow for control of the heat transfer from the catheter to automatically control the temperature of the patient or of the target region within the patient. The apparatus may include a blood channeling sleeve that directs body fluid over a heat exchanger where the body fluid's temperature is altered, and then is discharged out the distal end of the sleeve to a desired location, for example, cooled blood to the brain for neuroprotection. The catheter may be used alone or in conjunction with other heat exchangers to cool one region of a patient's body while heating another.

27 Claims, 20 Drawing Sheets

U.S. PATENT DOCUMENTS

| | | |
|---|---|---|
| 3,369,549 A | 2/1968 | Armao |
| 3,425,419 A | 2/1969 | Dato |
| 3,726,283 A | 4/1973 | Dye et al. |
| 3,788,328 A | 1/1974 | Alley et al. |
| 3,995,617 A | 12/1976 | Watkins et al. |
| 4,014,317 A | 3/1977 | Bruno |
| 4,038,519 A | 7/1977 | Foucras |
| 4,111,209 A | 9/1978 | Wolvek et al. |
| 4,246,932 A | 1/1981 | Raines |
| 4,298,006 A | 11/1981 | Parks |
| 4,378,797 A | 4/1983 | Osterholm |
| 4,445,500 A | 5/1984 | Osterholm |
| 4,445,886 A | 5/1984 | Osterholm |
| 4,470,407 A | 9/1984 | Hussein |
| 4,540,402 A | 9/1985 | Aigner |
| 4,661,094 A | 4/1987 | Simpson |
| 4,662,383 A | 5/1987 | Sogawa et al. |
| 4,672,962 A | 6/1987 | Hershenson |
| 4,686,085 A | 8/1987 | Osterholm |
| 4,701,166 A | 10/1987 | Groshong et al. |
| 4,705,501 A | 11/1987 | Wigners et al. |
| 4,748,979 A | 6/1988 | Hershenson |
| 4,750,493 A | 6/1988 | Brader |
| 4,754,752 A | 7/1988 | Ginsburg et al. |
| 4,762,130 A | 8/1988 | Fogarty et al. |
| 4,769,005 A | 9/1988 | Ginsburg et al. |
| 4,804,358 A | 2/1989 | Karcher et al. |
| 4,819,655 A | 4/1989 | Webler |
| 4,840,617 A | 6/1989 | Osterholm |
| 4,857,054 A | 8/1989 | Helfer |
| 4,892,095 A | 1/1990 | Nakhgevany |
| 4,892,519 A | 1/1990 | Songer et al. |
| 4,899,741 A | 2/1990 | Bentley et al. |
| 4,909,252 A | 3/1990 | Goldberger |
| 4,920,963 A | 5/1990 | Brader |
| 4,941,475 A | 7/1990 | Williams et al. |
| 4,960,103 A | 10/1990 | Urso |
| 4,976,691 A | 12/1990 | Sahota |
| 4,995,863 A | 2/1991 | Nichols et al. |
| 5,019,075 A | 5/1991 | Spears et al. |
| 5,030,210 A | 7/1991 | Alchas |
| 5,041,089 A | 8/1991 | Mueller et al. |
| 5,092,841 A | 3/1992 | Spears |
| 5,106,360 A | 4/1992 | Ishiwara et al. |
| 5,112,301 A | 5/1992 | Fenton, Jr. et al. |
| 5,147,385 A | 9/1992 | Beck et al. |
| 5,149,321 A | 9/1992 | Klatz et al. |
| 5,151,100 A | 9/1992 | Abele et al. |
| 5,174,285 A | 12/1992 | Fontenot |
| 5,180,364 A | 1/1993 | Ginsburg |
| 5,191,883 A | 3/1993 | Lennox et al. |
| 5,196,024 A | 3/1993 | Barath |
| 5,211,631 A | 5/1993 | Sheaff |
| 5,234,405 A | 8/1993 | Klatz et al. |
| 5,248,312 A | 9/1993 | Langberg |
| 5,250,070 A | 10/1993 | Parodi |
| 5,257,977 A | 11/1993 | Eshel |
| 5,261,399 A | 11/1993 | Klatz et al. |
| 5,269,758 A * | 12/1993 | Taheri ............... 604/96.01 |
| 5,342,301 A | 8/1994 | Saab |
| 5,344,436 A | 9/1994 | Fontenot et al. |
| 5,368,591 A | 11/1994 | Lennox et al. |
| 5,383,856 A | 1/1995 | Bersin |
| 5,395,314 A | 3/1995 | Klatz et al. |
| 5,403,281 A | 4/1995 | O'Neill et al. |
| 5,437,673 A | 8/1995 | Baust et al. |
| 5,486,208 A | 1/1996 | Ginsburg |
| 5,531,776 A | 7/1996 | Ward et al. |
| 5,584,804 A | 12/1996 | Klatz et al. |
| 5,624,392 A | 4/1997 | Saab |
| 5,653,692 A | 8/1997 | Masterson et al. |
| 5,716,386 A | 2/1998 | Ward et al. |
| 5,733,319 A | 3/1998 | Neilson et al. |
| 5,755,755 A | 5/1998 | Panyard |
| 5,908,407 A | 6/1999 | Frazee et al. |
| 5,957,963 A | 9/1999 | Dobak, III |
| 5,980,561 A | 11/1999 | Kolen et al. |
| 6,007,571 A | 12/1999 | Neilson et al. |
| 6,042,559 A | 3/2000 | Dobak, III |
| 6,051,019 A | 4/2000 | Dobak, III |
| 6,096,068 A | 8/2000 | Dobak, III et al. |
| 6,126,684 A * | 10/2000 | Gobin et al. ............... 607/113 |
| 6,149,677 A * | 11/2000 | Dobak, III ............... 607/106 |
| 6,231,595 B1 | 5/2001 | Dobak, III |
| 6,338,727 B1 | 1/2002 | Noda et al. |
| 6,497,721 B2 | 12/2002 | Ginsburg et al. |
| 6,527,798 B2 | 3/2003 | Ginsburg et al. |
| 6,620,188 B1 | 9/2003 | Ginsburg et al. |
| 6,635,076 B1 | 10/2003 | Ginsburg |

FOREIGN PATENT DOCUMENTS

| | | |
|---|---|---|
| WO | 9105528 | 2/1991 |
| WO | 9725011 | 7/1997 |
| WO | 9826831 | 6/1998 |
| WO | 00/09054 | 2/2000 |

OTHER PUBLICATIONS

Effects of Total Body Core Cooling on Heat Production of Conscious Goats; James B. Mercer & Claus Jessen; Pflugers Archiv European Journal of Physiology; Springer-Verlag 1978.

Safar, P., Dynamics of Brain Resuscitation After Ischemic Anoxia, Hospital Practice, Feb. 1981, pp. 67-72.

Gisvold, S., et al., Multifaceted Therapy After Global Brain Ischemia in Monkeys, Stroke, vol. 15, No. 5, Sep. 1984, pp. 803-812.

Leonov, Y. et al., Mild Cerebral Hypothermia during and After Cardiac Arrest Improves Neurologic Outcome in Dogs, Journal of Cerebral Blood Flow and Metabolism, vol. 10, 1990, pp. 57-70.

Minamisawa, H. et al., The Effect of Mild Hyperthermia and Hypothermia on Brain Damage Following 5, 10 and 15 Minutes of Forebrain Ischemia, American Neurological Association, 1990, pp. 26-33.

Tisherman, S. et al., Therapeutic Deep Hypothermic Circulatory Arrest in Dogs: A Resuscitation Modality for Hemorrahagic Shock with 'Irreparable' Injury, The Journal of Trauma, vol. 30, No. 7, Jul. 1990, pp. 836-847.

Tisherman, S. et al., Deep Hypothermic Circulatory Arrest Induced During Hemorrhagic Shock in Dogs: Preliminary Systemic and Cerebral Metabolism Studies, Current Surgery, Sep. 1990, pp. 327-330.

Leonov, Y. et al., Moderate Hypothermia After Cardiac Arrest of 17 Minutes in Dogs: Effect on Cerebral and Cardiac Outcome, Stroke, vol. 21, No. 11, Nov. 1990, pp. 1600-1606.

Sterz, F. et al., Mild Hypothermia Cardiopulmonary Resuscitation Improves Outcome after Prolonged Cardiac Arrest in Dogs, Critical Care Medicine, vol. 19, No. 3, 1991, pp. 379-389.

Tisherman, S. et al., Profound Hypothermia (<10° C) Compared with Deep Hypothermia (15° C) Improves Neurologic Outcome in Dogs After Two Hours' Circulatory Arrest Induced to Enable Resuscitative Surgery, The Journal of Trauma, vol. 31, No. 8, Aug. 1991, pp. 1051-1062.

Dietrich, W., The Importance of Brain Temperature in Celebral Injury, Journal of Neurotrauma, vol. 9, Suppl. 2, 1992, pp. S475-S485.

Ginsberg, M. et al., Therapeutic Modulation of Brain Temperature: Relevance to Ischemic Brain Injury, Cerebrovascular and Brain Metabolism Reviews, vol. 4, No. 3, 1992, pp. 189-225.

Martinez-Arizala, A. et al., Hypothermia in Spinal Cord Injury, Journal of Neurotrauma, vol. 9., Suppl. 2, 1992, pp. S497-S505.

Weinrauch, V. et al., Beneficial Effect of Mild Hypothermia and Detrimental Effect of Deep Hypothermia After Cardiac Arrest in Dogs, Stroke, vol. 23, No. 10, Oct. 1992, pp. 1454-1462.

Kunoyama, K, et al., Delay in Cooling Negates the Beneficial Effect of Mild Resuscitative Cerebral Hypothermia After Cardiac Arrest in Dogs: A Prospective, Randomized Study, Crit. Care Med., vol. 21, No. 9, 1993, pp. 1348-1358.

Maher, J. et. al., Hypothermia as a Potential Treatment of Cerebral Ischemia, Cerebrovascular and Brain Metabolism Reviews, vol. 5, No. 4, 1993, pp. 227-300.

Safar, P., Cerebral Resuscitation After Cardiac Arrest: Research Initiatives and Future Directions, Annals of Emergency Medicine, vol. 22, No. 2, Part 2, Feb. 1993, pp. 324-389.

Oku, K., et al., Mild Hypothermia After Cardiac Arrest in Dogs Does Not Affect Postarrest Multifocal Cerebral Hypoperfusion, Stroke, vol. 24, No. 10, Oct. 1993, pp. 1590-1597.

Kuboyama, K. et al., Mild Hypothermia After Cardiac Arrest in Dogs Does Not Affect Postarrest Cerebral Oxygen Uptake/Delivery Mismatching, Resuscitation, vol. 27, 1994, pp. 231-244.

Laptook, A. et al., Modest Hypothermia Provides Partial Neuroprotection for Ischemic Neonatal Brain, Pediatric Research, vol. 35, No. 4, 1994, pp. 436-442.

Salzano, Richard P., et al., Regional Hypothermia of the Spinal Cord Protects Against Ischemic Injury During Thoracic Aortic Cross-Clamping, The Society of Thoracic Surgeons, vol. 57, 1994, pp. 65-71.

Onoe, M. et al., The Effect of Pulsatile Perfusion on Cerebral Blood Flow During Profound Hypothermia with Total Circulatory Arrest, Journal of Thoracic and Cardiovascular Surgery, vol. 108, Jul. 1994, pp. 119-125.

Xiao, F. et al., Peritoneal Cooling for Mild Cerebral Hypothermia After Cardiac Arrest in Dogs, Resuscitation, vol. 30, 1995, pp. 51-59.

Sessler, D., Deliberate Mild Hypothermia, Journal of Neurosurgical Anesthesiology, vol. 7, No. 1, Jan. 1995, pp. 38-46.

Capone, A., et al., Complete Recovery After Normothermic Hemorrahagic Shock and Profound Hypothermic of 60 Minutes in Dogs, The Journal of Trauma: Injury, Infection and Critical Care, vol. 40, No. 3, 1996, pp. 388-395.

Gisvold, S. et al., Cerebral Resuscitation form Cardiac Arrest: Treatment Potentials, Crit. Care Med., vol. 24, No. 2 Suppl., 1996, pp. S69-S80.

Kataoka, K. et al., Ischemic Neuronal Damage: How Does Mild Hypothermia Modulate It?, Molecular and Chemical Neuropathology, vol. 28, 1996, pp. 191-195.

Safar, P., et al., Selective Brain Cooling After Cardiac Arrest, Crit. Care Med., 1996, vol. 24, No. 6, pp. 911-914.

Sterz, F. et al., Mild Resuscitation Hypothermia and Outcome After Cardiopulmonary Resuscitation, Journal of Neurosurgical Anesthesiology, vol. 8, No. 1, 1996, pp. 88-96.

Wass, C. et al., Hypothermia-Associated Protection from Ischemic Brain Injury: Implications for Patient Management, International Anesthesiology Clinics: Topics in Neuroanesthesia, vol. 34, No. 4, 1996, pp. 95-111.

Safar, P. et al., Improved Cerebral Resuscitation From Cardiac Arrest in Dogs With Mild Hypothermia Plus Blood Flow Promotion, Stroke, vol. 27, No. 1, Jan. 1996, pp. 105-113.

Marion, D. et al., Resuscitative Hypothermia, Crit. Care Med., vol. 24, No. 2, Suppl., Feb. 1996, pp. S81-S89.

Rosomoff, H. et al, Resuscitation From Severe Brain Trauma, Crit. Care Med., vol. 24, No. 2, Suppl. Feb. 1996, pp. S48-S56.

Markarian, G. et al., Mild Hypothermia: Therapeutic Window After Experimental Cerebral Ischemia, Neurosurgery, vol. 38, No. 3, Mar. 1996, pp. 542-551.

Hoffman, W. et al., Effects of Graded Hypothermia on Outcome From Brain Ischemia, Neurological Research, vol. 18, No. 2, Apr. 1996, pp. 185-199.

Schwartz, A. et al., Isolated Cerebral Hypothermia by Single Carotid Artery Perfusion of Extracorporeally Cooled Blood in Baboons, Neurosurgery, vol. 39, No. 3, Sep. 1996, pp. 577-582.

Metz, C. et al, Moderate Hypothermia in Patients With Severe Head Injury: Cerebral and Extracerebral Effects, Journal of Neurosurgery, vol. 85, No. 4, Oct. 1996, pp. 533-541.

Barone, F. et al., Brain Cooling During Transient Focal Ischemia Provides Complete Neuroprotection, Neuroscience and Biobehavioral Reviews, vol. 21, No. 1, pp. 31-44, 1997.

Tisherman, S. et al., Future Directions for Resuscitation Research, V. Ultra-Advanced Life Support, Resuscitation, vol. 34, 1997, pp. 281-293.

Colbourne, F. et al., Postischemic Hypothermia: A Critical Appraisal with Implications for Clinical Treatment, Molecular Neurobiology, vol. 14, No. 3, Jun. 1997, pp. 171-201.

Long, R., Regional Cranial Hypothermia in the Prevention of Cerebral Ischemic Damage During Carotid Occlusion, Review of Surgery, vol. 23, No. 3, May 1966, pp. 226-228.

White, R., et al., Profound Selective Cooling and Ischemia of Primate Brain Without Pump or Oxygenator, Surgery, vol. 66, No. 1, Jul. 1969, pp. 224-232.

Weale, F.E., The Aneroid Manometer in Peripheral Arterial Surgery, The British Journal of Surgery, vol. 56, No. 8, Aug. 1969, pp. 612-631.

Negrin, Jr., J., The Hypothermostat: An Instrument to Obtain Local Hypothermia of the Brain or Spinal Cord, International Surgery, Sec. 1, vol. 54, No. 2, Aug. 1970, pp. 93-106.

Safar, P., Resuscitation After Global Brain Ischemia-Anaxia, Crit. Care Med., vol. 6, No. 4, 1978, pp. 215-227.

Ping, F. et al., Protection of the Brain From Hypoxia: A Review, Canad. Anaesth. Soc. J., vol. 25, No. 6, Nov. 1978, pp. 468-473.

* cited by examiner

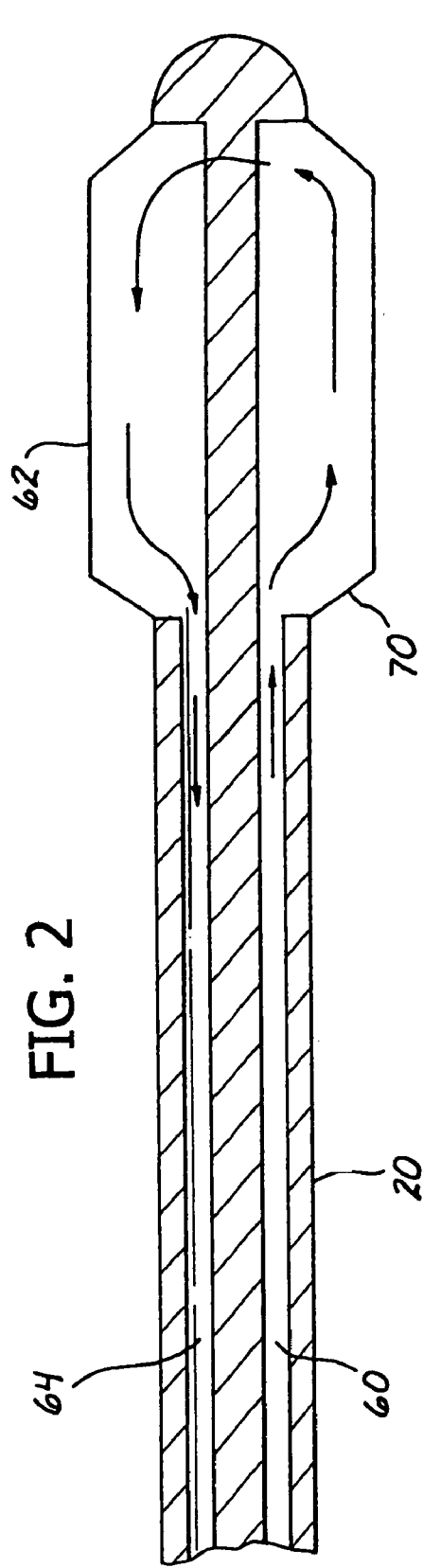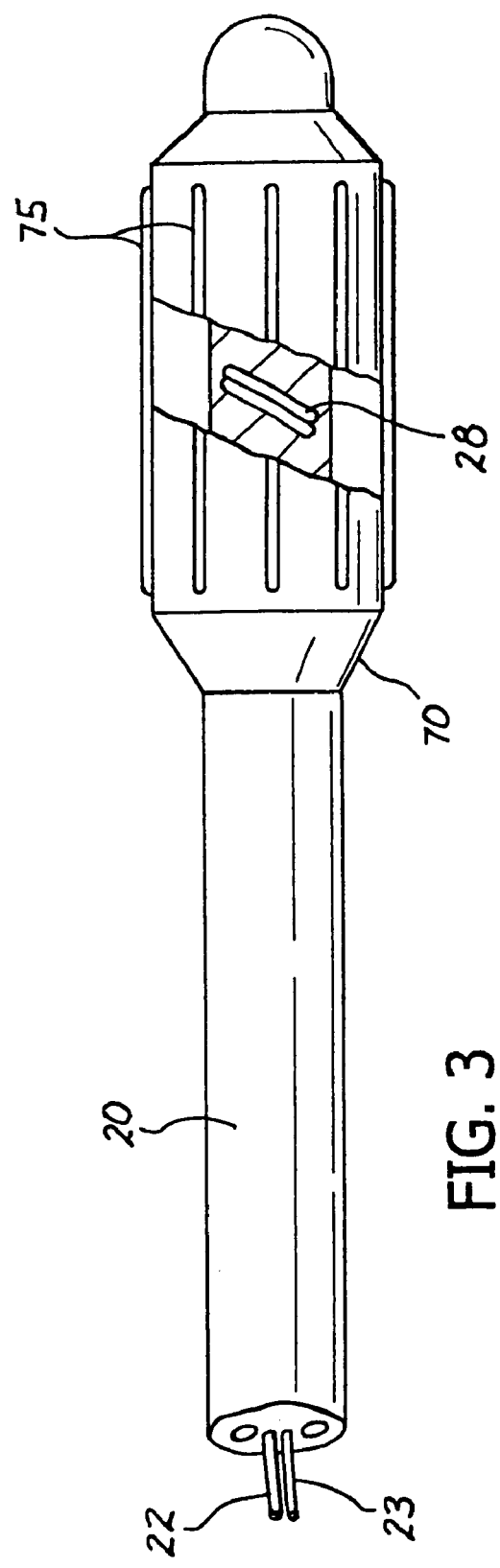
FIG. 2
FIG. 3

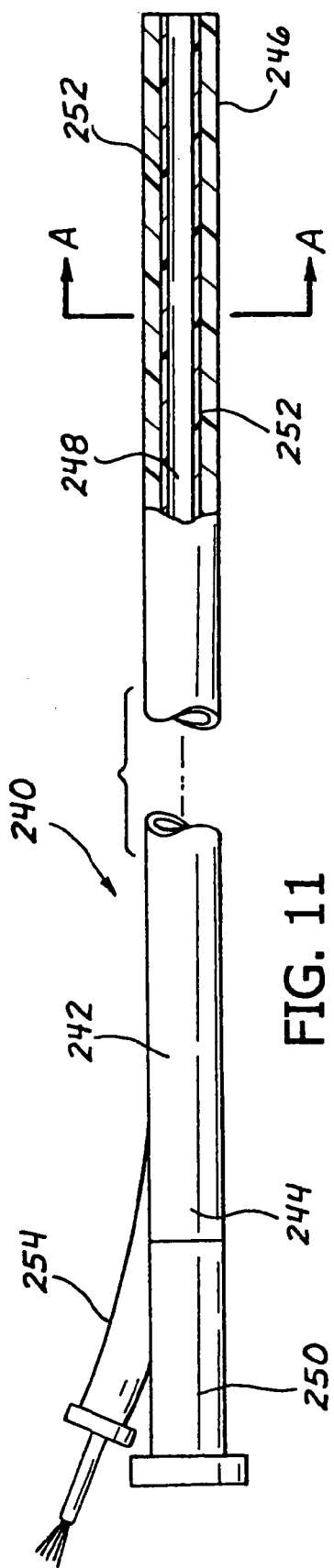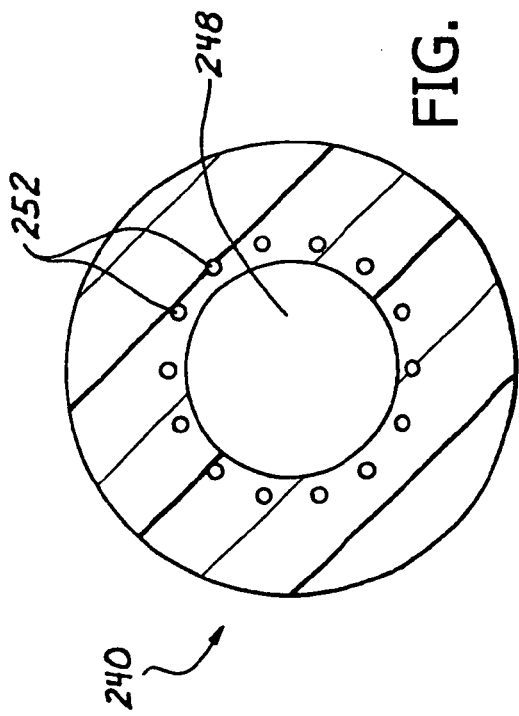
FIG. 11
FIG. 11A

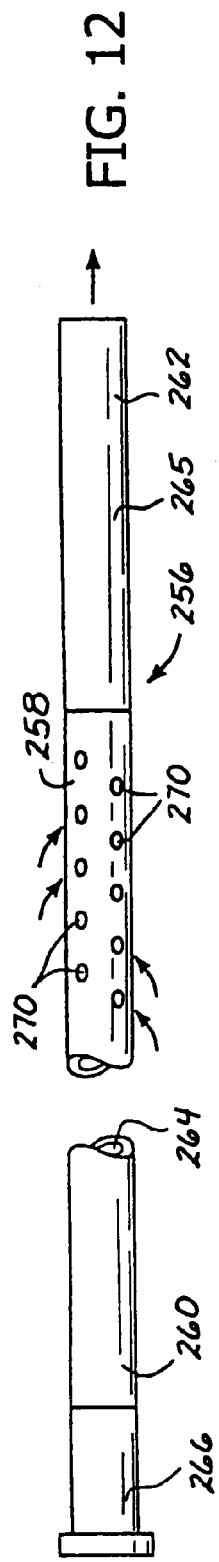
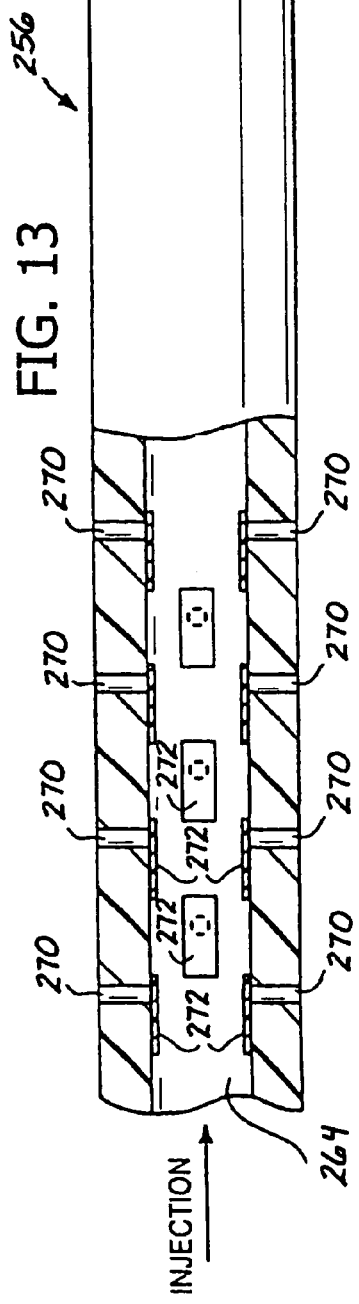
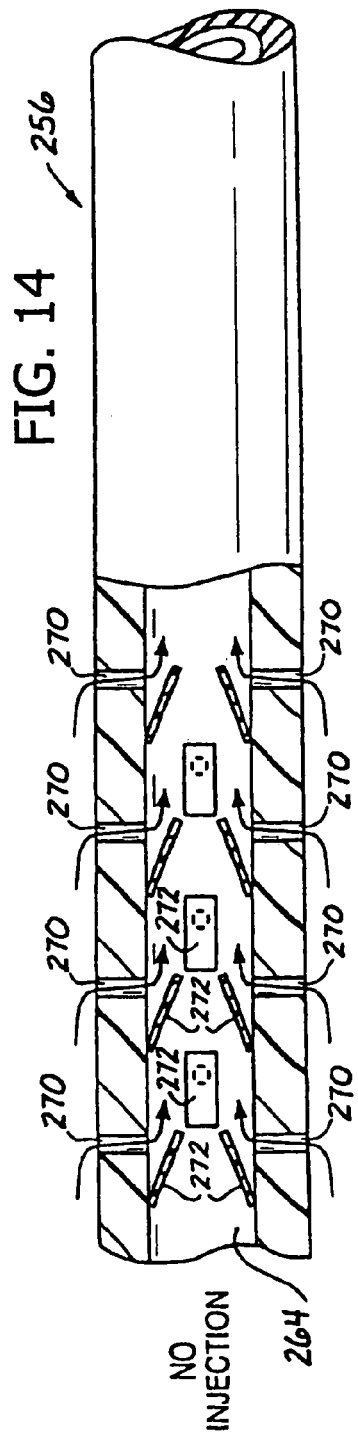
FIG. 12
FIG. 13
FIG. 14

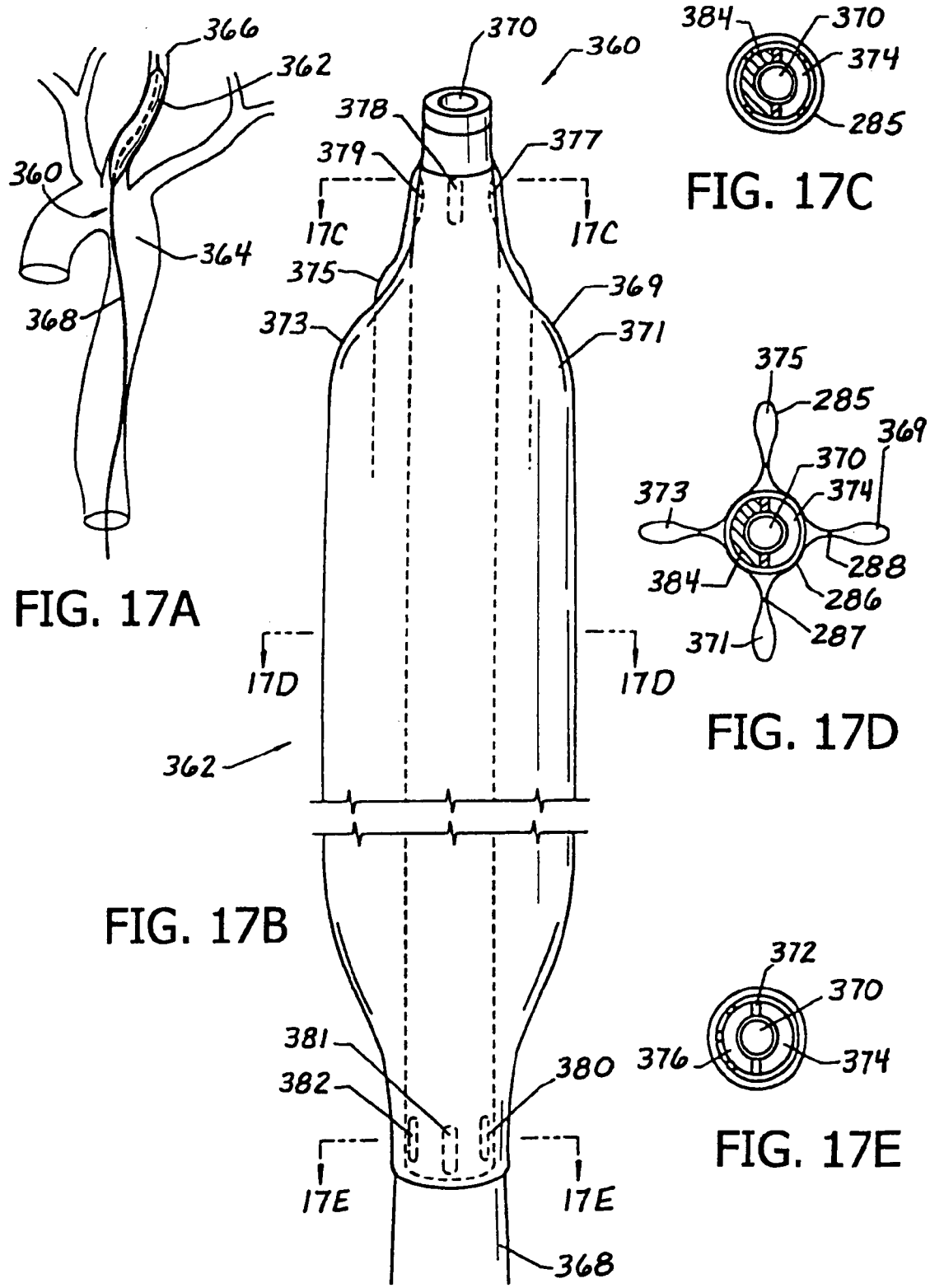

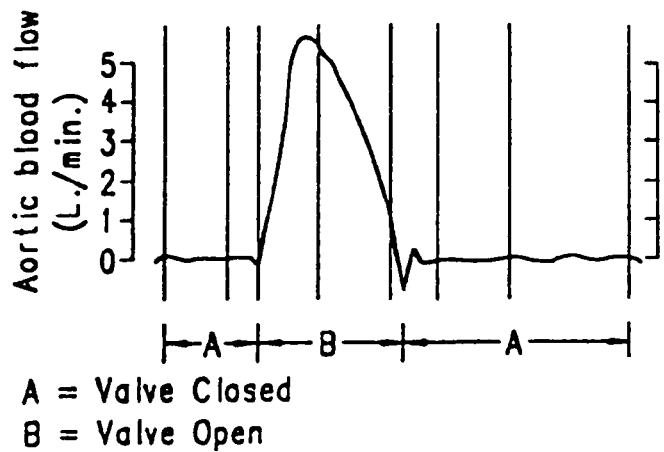
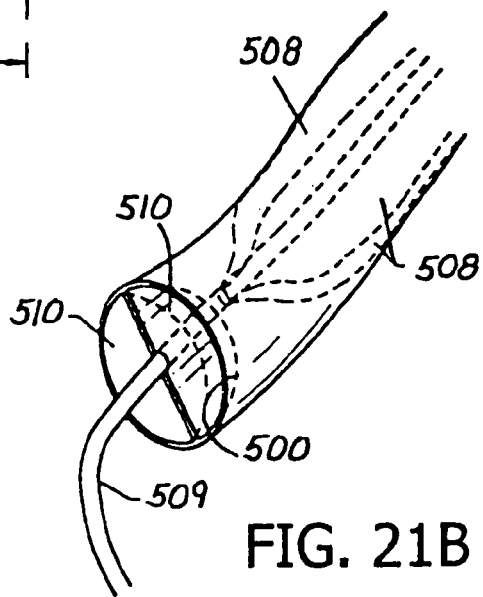
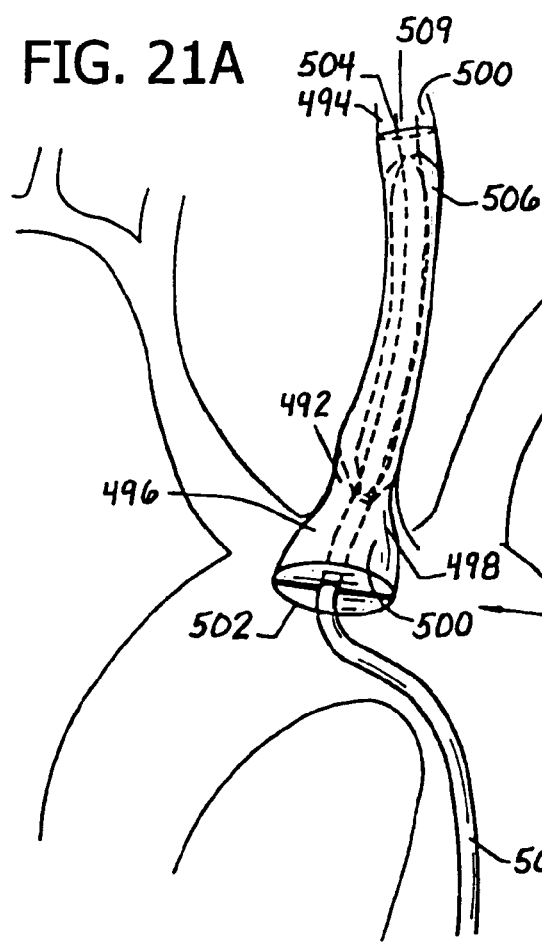
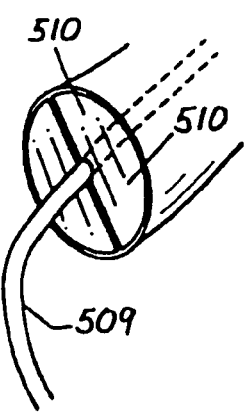
FIG. 21D
FIG. 21B
FIG. 21A
FIG. 21C

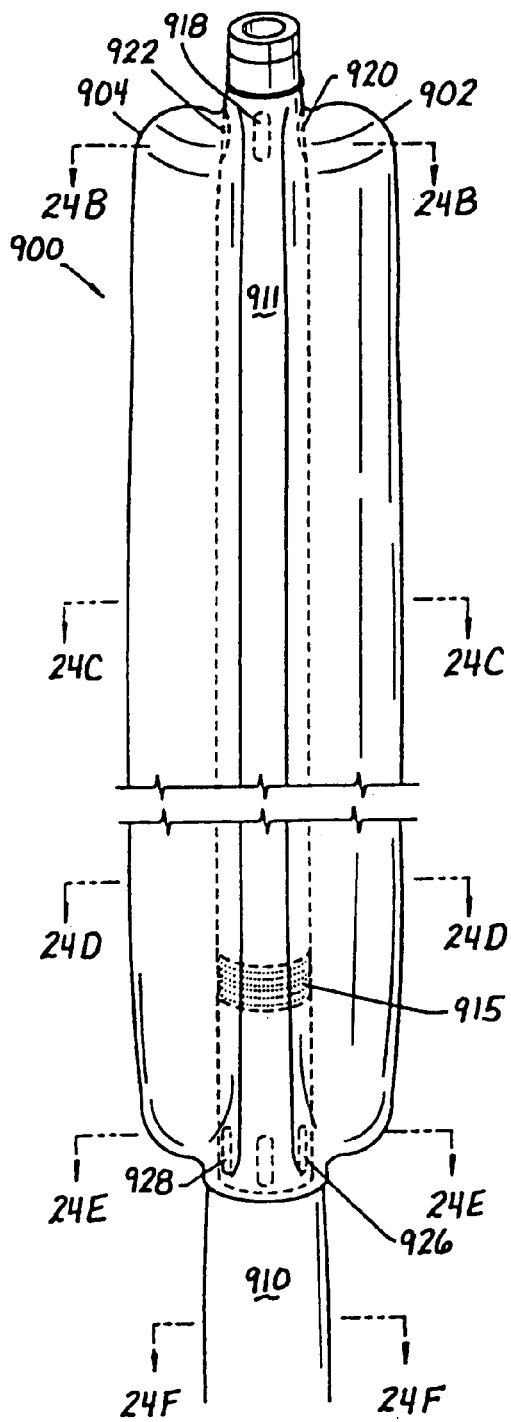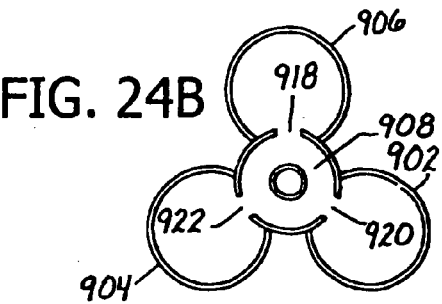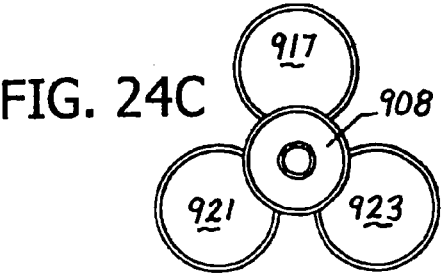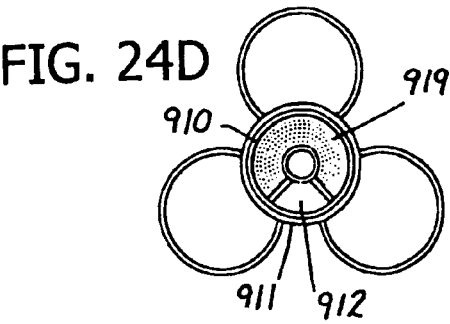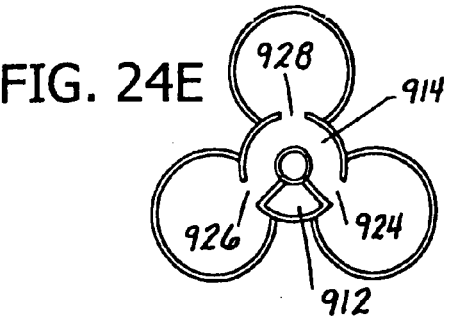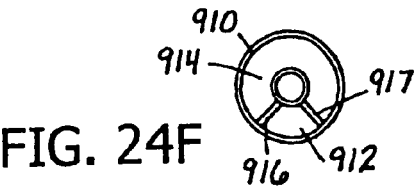

METHODS AND APPARATUS FOR REGIONAL AND WHOLE BODY TEMPERATURE MODIFICATION

RELATED APPLICATION

This is a continuation of U.S. patent application Ser. No. 10/626,007 filed Jul. 24, 2003 now U.S. Pat. No. 7,217,282, which is a continuation of Ser. No. 09/138,830 filed Aug. 24, 1998 now issued as U.S. Pat. No. 6,620,188, which is a continuation in part of Ser. No. 08/584,013 filed Jan. 8, 1996 now issued as U.S. Pat. No. 5,837,003, which is a continuation in part of Ser. No. 08/324,853 filed Oct. 18, 1994 now issued as U.S. Pat. No. 5,486,208, which is a continuation of Ser. No. 08/015,714 filed Feb. 9, 1993, the entire disclosures of each such related patent application being expressly incorporated herein by reference.

FIELD OF THE INVENTION

The present invention generally relates to the selective modification and control of a patient's body temperature, and to the regulation of the temperature of a fluid that is to be delivered to a specific target location within a body structure. More particularly, the invention provides methods and apparatus for treating or inducing hypothermia or hyperthermia by inserting a catheter into a blood vessel of the patient and selectively transferring heat to or from blood flowing through the vessel, and for altering the temperature of a fluid that is to be delivered to the target location while the fluid is within the patient.

The present invention further relates to the selective modification and control of whole body temperature and the temperature of selected target regions of the body such as the brain. More particularly, the invention is directed to methods and apparatus for lowering the temperature of the brain by using heat transfer regions of a heat transfer catheter to cool fluids in contact with, or circulating in, around, or leading to the brain region to provide regional hypothermia and temperature control.

BACKGROUND OF THE INVENTION

Under ordinary circumstances, the thermal regulatory system of the human body maintains a near constant temperature of about 37° C. (98.6° F.). Heat lost to the environment is precisely balanced by internal heat produced within the body.

Hypothermia is a condition of abnormally low body temperature generally characterized by a core body temperature of 35° C. or less, and may be further clinically defined according to its severity. For example, a body core temperature within the range of 32° C. to 35° C. may be described as mild hypothermia, 30° C. to 32° C. as moderate, 24° C. to 30° C. as severe, and a body temperature of less than 24° C. may constitute profound hypothermia. Although the above ranges may provide a useful basis for discussion, they are not absolutes and definitions vary widely as indicated in the medical literature.

Hyperthermia may be defined as a condition of abnormally high body temperature, and may be the result from exposure to a hot environment or surroundings, overexertion, or fever. Body core temperatures may range from 38° C. to 41° C. due to conditions such as fever, and may be substantially higher in cases of exposure and overexertion. Like hypothermia, hyperthermia is a serious condition that can be fatal.

Although both hypothermia and hyperthermia may be harmful and require treatment in some case, in other cases hyperthermia or hypothermia, and particularly hypothermia, may be therapeutic or otherwise advantageous, and therefore may be intentionally induced. For example, periods of cardiac arrest in the setting of myocardial infarction and heart surgery can produce brain damage or other nerve damage. Hypothermia is recognized in the medical community as an accepted neuroprotectant during cardiovascular surgery and therefore a patient is often kept in a state of induced hypothermia during cardiovascular surgery. Likewise, hypothermia is sometimes induced as a neuroprotectant during neurosurgery. Hypothermia may also be beneficial in other situations, for example, for victims of head trauma, spinal trauma, brain attack (also sometimes called stroke), spinal surgery or surgery where blood flow may be interrupted or compromised to the brain or spinal cord such as aneurysm repair, as well as other types of surgery where neuroprotection is desirable.

Neural tissue, that is all tissue of the nervous system such as the brain or spinal cord, is particularly subject to damage by vascular disease processes including, but not limited to ischemic or hemorrhagic stroke, blood deprivation for any reason, including cardiac arrest, intracerebral hemorrhage and head trauma. In each of these instances, damage to brain tissue may occur because of ischemia, pressure, edema or other processes resulting in a loss of cerebral function and permanent neurological deficits. Lowering the brain temperature may confer neuroprotection through several mechanisms including the blunting of post-insult elevation of neurotransmitters such as glutamate, reduction of cerebral metabolic rate, moderation of intracellular calcium, prevention of intracellular protein synthesis inhibition, and reduction of free radical formation as well as other enzymatic cascades and even genetic responses. Thus intentionally induced hypothermia may prevent some of the damage to brain or other neurological tissue during surgery or as a result of stroke, intracerebral hemorrhage and trauma.

Treatment of stroke in particular is a possibly therapeutic use of intentionally induced hypothermia. Stroke (sometimes called brain attack) is a severely debilitating and complex disease that results from the blockage (ischemic stroke) or rupture (hemorrhagic stroke) of a blood vessel within or leading to the brain region. During a stroke, brain cells are damaged either by a lack of oxygen or by increased pressure. These events can eventually result in death and necrosis of brain tissue. In general, at least one goal in the therapeutic intervention for stroke is to preserve the function of as much brain tissue as possible. However, current medical treatment for stroke is largely supportive in nature. Newer treatments, for example clot-dissolving drugs, are available but may be only suitable for treatment of ischemic strokes and must generally be used shortly (within several hours) of the initial stroke symptoms to avoid side effects related to bleeding within the brain. In practice, it has been difficult to treat strokes within this time window since patients often do not arrive at a medical facility until several hours after the onset of a stroke. As a result, most strokes are not aggressively treated with medical therapy. A treatment to prolong this time window, and to protect brain cells from death, would have a profound impact on patient care.

Experimental studies of ischemia have shown reduction in infarcted brain tissue volume in animals treated with hypothermia during or shortly after a stroke or ischemic insult. It is therefore believed that the application of hypothermia to a patient who is suffering or has recently suffered a stroke may be beneficial.

Despite the acceptance of hypothermia as a neuroprotectant, it has not been widely used outside of the surgical setting. Additionally, most current practices attempt to provide hypothermia to the brain by inducing whole body hypothermia through systemic treatment. However, whole body hypothermia presents numerous difficulties and is cumbersome to implement in a patient who is not under general anesthesia. Lowering the systemic temperature of a patient not only takes a significant amount of time, but also subjects the patient to deleterious effects of hypothermia including cardiac arrhythmias, coagulation problems, increased susceptibility to infections, and problems of discomfort such as profound shivering.

Control of the body's temperature, for example, to maintain normothermia (usually 37° C.), is often desirable. For example, in a patient under general anesthesia, the body's normal temperature regulating mechanisms may not be fully functioning, and the anesthesiologist may be required to artificially control the patient's body temperature. Similarly, a patient may lose an extraordinary amount of heat to the environment, for example, during major surgery, and the patient's unaided body may not be able to generate sufficient heat to compensate for the heat lost. A device and method for controlling body temperature, for example by adding heat to maintain normothermia, would be desirable.

Particularly in the surgical setting, it has sometimes been the case that blood or other fluid was heated or cooled outside a patient's body and introduced into the body to heat or cool the body or some target location within the body. However, heating or cooling fluids outside of the patient may be cumbersome and require elaborate equipment. For example, in surgery, the temperature of a patient may be controlled by a bypass machine where a significant amount of the patient's blood is removed, heated or cooled outside the body in a by-pass machine, and reintroduced to the patient's blood stream. One particular application of this procedure is whole body hypothermia sometimes induced during heart surgery. Other examples include hypothermia induced during neurosurgery or aortic or other vascular surgery.

The use of an external method for inducing hypothermia, such as a bypass machine, is an extremely invasive procedure that subjects vast quantities of the patients' blood to pumping for an extended length of time. External pumping of blood may be harmful to the blood, and continued pumping of blood into a patient for extensive periods of time, for example, more than one or two hours, is generally avoided. Additionally, such a procedure may require systemic treatment of the patient, for example, with heparin to prevent clotting which may present other undesirable consequences in a stroke victim.

Means of imparting heat to the blood of a patient, or removing heat from the patient, which do not require external pumping have been proposed. For example, one particular catheter structure which has been developed to treat patients suffering from either hypothermia or hyperthermia is described in U.S. Pat. No. 5,486,208, to Ginsburg, the complete disclosure of which is herein incorporated by reference. That patent issued from one of the applications from which this application claims priority. A catheter disclosed in that patent was inserted into a blood vessel and a portion of the catheter heated or cooled, transferring heat to the patient's blood and thereby affecting the overall body temperature of the patient. However, while such devices and methods may avoid the problems associated with external pumping of blood, they do not eliminate the difficulties that arise when the entire body is subjected to hypothermia.

There have been attempts to achieve regional cerebral hypothermia, for example by placing the head in a cooled helmet or shroud, or even injecting a cold solution into the head region. Attempts to achieve brain cooling by directly cooling the surface of the head have proven impractical or ineffective because of factors such as the insulating qualities of the skull, which make it difficult to effectively lower brain core temperature, and the blood flow that may fail to provide sufficient heat transfer circulation to the brain itself when the surface of the head is cooled. Patients, especially patients not under general anesthesia, may also find it difficult to tolerate immersion or direct exposure of the head to a cold solution or cooling surface.

An apparatus to facilitate transfer of heat to or from a target location by means of internally applied heating or cooling would be advantageous. It has been known in the art to impart heat by direct contact with specific tissue by means of a balloon catheter. For example, in U.S. Pat. No. 5,019,075 to Spears, a heated balloon was described to apply heat directly from the surface of the balloon to the wall of an artery dilated during percutaneous transluminal coronary angioplasty (PTCA) to fuse together disrupted tissue. This device, however, operated by direct contact between the vessel wall in question and a greatly heated balloon surface.

Balloons capable of acting as ongoing heat transfer balloons by the continual flow of heat transfer medium through the balloon have also been shown. For example, in U.S. Pat. No. 5,624,392 to Saab, a concentric inflow and outflow lumen each terminate within the heat transfer balloon so that a continual flow of heat transfer liquid can be maintained within the balloon for controlled heat transfer to the adjacent tissue.

U.S. Pat. No. 5,269,758 to Taheri, discloses a balloon in which heated fluid such as heated saline solution is circulated through a balloon that pulses. The heat from the heat transfer liquid may then be imparted to the blood as it flows past the balloon to treat hypothermia in a patient. The flow of the affected blood is not otherwise generally directed nor is the temperature of a target region disclosed to be altered by the heated balloon of Tahari.

The configuration of balloons to provide channels for the flow of blood from the proximal side to the distal side of a balloon blocking a blood vessel, such as a balloon used for PTCA has also been shown. For example, such an autoperfusion balloon angioplasty catheter is shown in U.S. Pat. No. 4,581,017 to Sahota, and the multi-lumen balloon shown in U.S. Pat. No. 5,342,301 to Saab as discussed for use in angioplasty discloses a multi-lumen balloon catheter configured to allow blood to perfuse from the proximal side to the distal side of a balloon angioplasty catheter when the balloon is inflated to apply angioplastic pressure against the blood vessel walls and otherwise fully obstruct blood passage.

It would be desirable to devise an apparatus capable of heating or cooling liquid such as blood within the body and directing that liquid after it is heated or cooled, to a target location. It would be particularly advantageous if a device could be devised where the liquid could be directed to a desired location using only the patient's own heart as a pump. It would also be particularly advantageous if a method could be devised for directing heated or cooled blood to a target region of a patient's body for a sufficient length of time to affect the temperature of that target region.

A method of treating a patient to protect tissue, and particularly neural tissue, by inducing hypothermia is desirable. Protecting particular target tissue by inducing hypothermia in that tissue by means of in situ cooling of body fluid directed to that tissue would be particularly advantageous.

It would also be desirable to provide a system to control such a device to perform the method of treatment in a simple and predictable manner. It would be particularly desirable if such a system could control the device in conjunction with feedback data from a patient to control the device to predictably and selectively affect the temperature of a target region in the patient.

SUMMARY OF THE INVENTION

The present invention provides heat exchange catheter devices which generally comprise an elongate flexible catheter having a heat exchanger which is operative to exchange heat between blood or other body fluid which flows in heat exchanging proximity thereto. Also, the present invention provides methods for utilizing such heat exchange catheter devices to selectively heat or cool a particular region (e.g., the brain, a selected portion of the brain, the spinal cord, an organ, an intra-abdominal organ, the spleen, the liver, the heart, a portion of the heart, a lung, a kidney, a muscle, a tumor, a site where trauma has occurred, a site where hemorrhage has occurred, etc.) of the body of a mammalian patient.

In accordance with the devices of the present invention; there is provided a heat exchange catheter device which may generally comprise: i) an elongate catheter having a proximal end and a distal end, the entire length of said flexible catheter being defined as the distance from its proximal end to its distal end; ii) at least one fluid lumen through which a thermal exchange fluid may be circulated, and, iii) a heat exchanger with heat exchange fins located at a first location on the catheter, and a working lumen extending from outside the patient through at least part of the catheter that is inserted into the patient. The heat exchanger is operative to exchange heat between blood which flows in heat exchanging proximity to the heat exchanger and a thermal exchange fluid which is circulated through the catheter. The "first location" at which the heat exchanger is located may constitute less than the entire length of the catheter, and is typically at or near the distal end of the catheter. The heat exchanger may specifically comprise a balloon or other structure through which the thermal exchange fluid may circulate, and the heat exchange fins may be a plurality of lobes of the balloon or may be surface area increasing projections (e.g., outwardly extending protuberances, ribs, etc.) to enhance the efficiency with which heat exchange occurs. Also, in some embodiments of the catheter device, a body fluid channeling sleeve may be formed about the portion of the catheter whereupon the heat exchanger is located (and may extend some distance proximal to the heat exchanger) to channel a flow of blood or other body fluid in heat exchanging proximity to the heat exchanger. Such body fluid channeling sleeve may thus be utilized to channel available body fluid (e.g., blood) form one anatomical conduit (e.g., the descending aorta) in which the proximal end of the sleeve is located, into a second anatomical conduit (e.g., a carotid artery) in which the distal end of the sleeve is located. The sleeve may be sized and configured to form a shoulder that forms a snug seal between the outside of the sleeve and the second anatomical conduit.

The catheter device may further be provided in combination with a device (such as a guide wire, or embolectomy catheter) or medicament (such as a thrombolytic agent or barbiturate) for insertion through the working lumen.

The catheter device of the invention may also comprise a curved heat exchange balloon with an insulated side and a thermoconductive side, and may be placed in the anatomy such that blood flowing to the brain flows past the thermoconductive side and blood flowing to the rest of the body flows past the insulated side.

Finally, another aspect of the invention is the catheter device in combination with a control system that senses body conditions such as temperature and controls the catheter in response to the body conditions sensed, such as turning off the heat exchanger when the patient's target region reaches a pre-selected temperature, or reactivating the heat exchanger when the temperature strays from that pre-selected temperature.

In accordance with the methods of the present invention, there is provided a procedure for modulating or changing the temperature of a selected region of the body of a mammalian patient. Such method comprises the steps of:

a. inserting a catheter device of the foregoing character into an anatomical conduit of the patient's body through which a body fluid flows to the selected region of the patient's body, and positioning the catheter such that body fluid flowing through the anatomical conduit to the selected region will pass in heat exchanging proximity to the heat exchanger before reaching said selected region; and, b. utilizing the heat exchanger of the catheter device to change the temperature of body fluid which passes in heat exchanging proximity to the heat exchanger, such that said body fluid will subsequently change the temperature of said selected region of the patient's body.

Still further in accordance with the methods of the present invention, the catheter device may be positioned in a blood vessel which leads to the brain (e.g., the right common carotid artery, left common carotid artery, innominate artery, right internal carotid artery, left internal carotid artery, etc.) and used to cool the brain or a portion thereof to deter neural damage following a stroke or other insult (e.g., period of ischemia, period of hypoxia, hemorrhage, trauma, etc.).

Still further in accordance with the methods of the present invention, two or more catheter devices of the foregoing character may be simultaneously positioned at different sites within the patient's body so as to selectively heat or cool body fluid (e.g., blood) which is flowing to the selected body region, and to subsequently return such body fluid to or close to its original temperature as it flows from the selected body region. In this regard, one heat exchange catheter device may be positioned in an artery which perfuses the brain to cause cooling of the brain following a stroke or other insult, and a second catheter may be positioned in the inferior vena cava or other suitable vein to re-warm blood after it circulates through the brain, or to generally add heat to blood going to the trunk of a patient's body to maintain normothermia in the body at locations other than the cooled region.

Another aspect of the invention provides a method of controlling the heat exchange with the body fluid such that a predetermined temperature may be established at a target tissue, and may be maintained. As an additional aspect, a predetermined temperature may be established for the target tissue, for example a particular hypothermic temperature for the brain, and another temperature may be selected for another region, for example the core body temperature being normothermic, and two catheters may be simultaneously controlled to maintain both pre-selected temperatures.

Further aspects and details of the present invention will become apparent to those of skill in the relevant art upon reading and understanding of the detailed description of preferred embodiments set forth here below. Each of the embodiments disclosed below may be considered individually or in combination with any of the other variations and aspects of the invention.

BRIEF DESCRIPTION OF THE DRAWINGS

FIG. 2 depicts a catheter in which a heated or cooled fluid flows through a balloon, which provides for an increased surface area near the distal end of the catheter.

FIG. 3 depicts a catheter having a resistance heating element at its distal end and a balloon having longitudinal ribs to further increase the heat transfer surface area.

FIG. 11 is a side view of an alternative catheter for heating a fluid passing through an internal lumen according to the invention.

FIG. 11A is a side view of the catheter of FIG. 11 taken along lines A-A.

FIG. 12 is a side view of another alternative embodiment of a catheter for heating or cooling a fluid passing through an internal lumen and having a plurality of perfusion orifices for allowing body fluids to enter into the internal lumen according to the invention.

FIG. 13 is a cutaway side view of a portion of a catheter similarly illustrated in FIG. 12 showing a plurality of flaps which are closed to prevent body fluids from entering into the internal lumen when a liquid is externally injected into the lumen.

FIG. 14 illustrates a catheter similarly illustrated in FIG. 13 showing the flaps opening to allow body fluids to enter into the internal lumen when no fluids are externally injected into the lumen.

FIG. 17A is a simplified perspective view of a variation of the heat transfer catheter of the invention in place within the left common carotid artery.

FIG. 17B is a simplified perspective view of the distal portion of a finned thermal balloon catheter in accordance with one aspect of the invention having a balloon heat transfer portion for supporting the circulation of heat transfer fluid.

FIG. 17C is a simplified cross-sectional view of the catheter illustrated in FIG. 17B taken along line C-C.

FIG. 17D is a simplified cross-sectional view of the catheter illustrated in FIG. 17B taken along line D-D.

FIG. 17E is a simplified cross-sectional view of the catheter illustrated in FIG. 17B taken along line E-E.

FIG. 18C is a simplified cross-sectional view of the catheter illustrated in FIG. 18B taken along line C-C.

FIG. 21A is a simplified perspective view of another variation of the thermal catheter formed with an occlusive shoulder and valve assembly.

FIG. 21B illustrates a proximal or distal sleeve valve in a closed position for a thermal catheter of the type shown in FIG. 21A.

FIG. 21C illustrates a proximal or distal sleeve valve in an open position for a thermal catheter of the type shown in FIG. 21A.

FIG. 21D provides a graphical representation of a heartbeat cycle with aortic blood flow measured against the synchronous opening and closing of a sleeve valve similarly shown in FIGS. 21A-C.

FIG. 24A is a simplified perspective view of a finned thermal balloon catheter, the fins being inflatable balloon lobes.

FIG. 24B is a simplified cross-sectional view taken along the line B-B in FIG. 24A.

FIG. 24C is a simplified cross-sectional view taken along the line C-C in FIG. 24A.

FIG. 24D is a simplified cross-sectional view taken along the line D-D in FIG. 24A.

FIG. 24E is a simplified cross-sectional view taken along the line E-E in FIG. 24A.

FIG. 24F is a simplified cross-sectional view taken along the line F-F in FIG. 24A.

DETAILED DESCRIPTION OF THE INVENTION

The present invention provides methods and apparatus for selectively controlling regional and whole body temperature by warming or cooling a body fluid such as blood in situ and directing the warmed or cooled body fluid to a desired location. According to the present invention, a catheter having a heat exchanger which may be, for example, a balloon with fins, is inserted into a fluid containing portion of the patients body, for example, a blood vessel. A blood channeling sleeve is mounted over the heat exchanger and is open at both its proximal end (closest to the insertion point) and its distal end (farthest along the catheter from the insertion point). The distal end of the sleeve is placed so that fluid such as blood that enters the proximal end of the sleeve flows in heat transfer proximity past the heat exchanger. Heat exchange proximity requires sufficient proximity for effective heat exchange to occur and depends on such factors as the chemical and physical make-up of the blood, the rate of flow past the heat exchange surface, the pattern of blood flow past the heat exchanger, (laminar flow, turbulent flow, and the like), the difference in temperature between the heat exchange surface and the blood, the material of which the heat exchange surface is made, and the proximity between the heat exchange surface and the blood. Fluid exits the distal end of the sleeve so that the heated or cooled blood is discharged in a desired location, for example upstream of target tissue such as the brain. By continuing to heat or cool fluid flowing to the target tissue for a sufficient length of time, the temperature of the target tissue is altered.

Likewise, when inducing hypothermia or hyperthermia, the invention provides for heating or cooling the target tissue to the desired temperature and maintaining that temperature by controlling the heat exchange catheter. Similarly, different regions may be controllably maintained at temperatures different from each other by controlling different heat exchange catheters at different locations with the patient's body. Additionally, the temperature of the target tissue may be maintained at a desired temperature, for example, mildly hypothermic, while the core temperature of the body may be monitored and maintained at a different temperature, for example, normothermic (37° C.) or nearly normothermic, by use of a separate heat exchange catheter or an additional heat exchange region located on the same heat exchange catheter.

Figure 1:
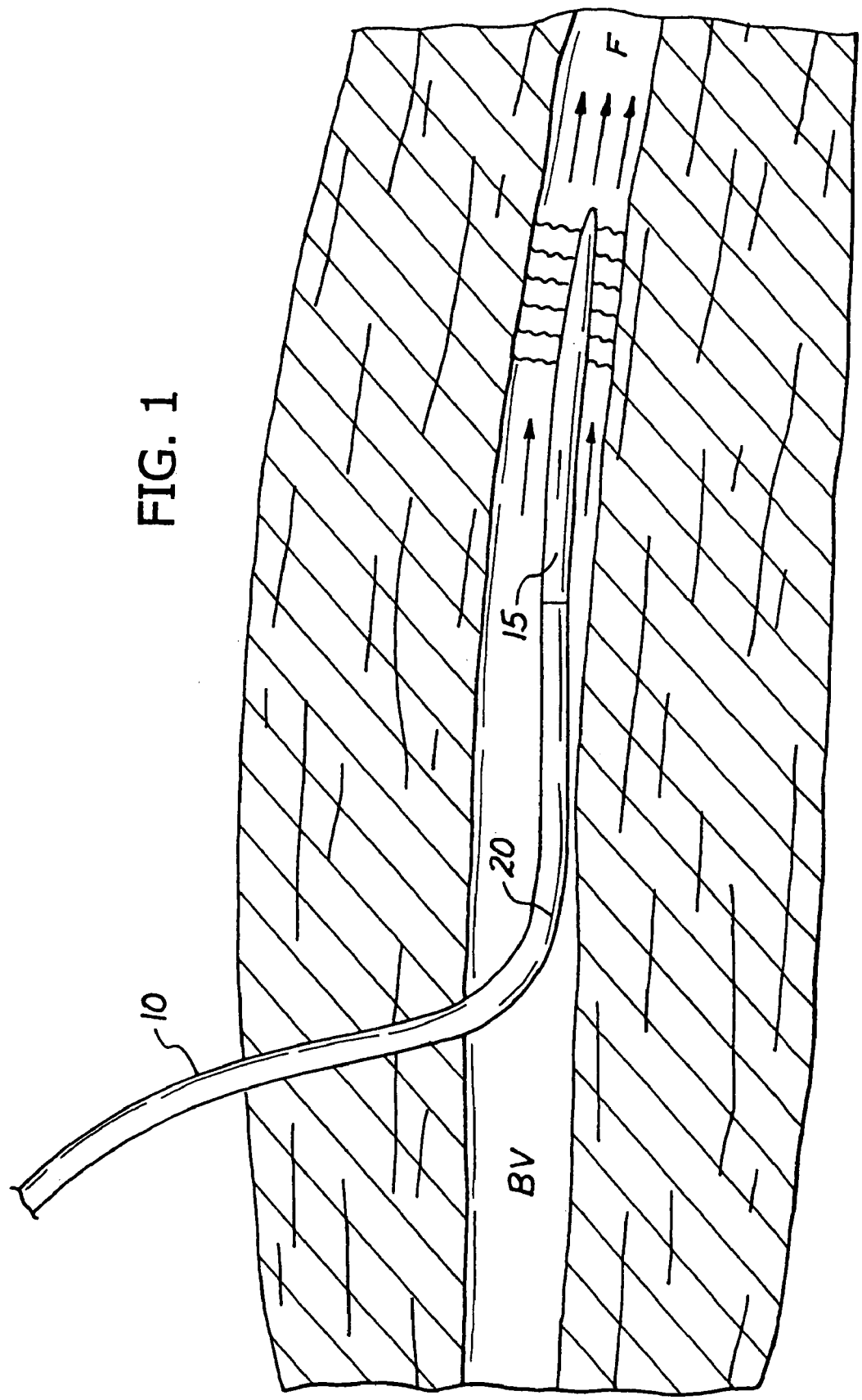
FIG. 1 depicts a catheter according to the present invention inserted percutaneously into a blood vessel of a patient.
Figure 4A:
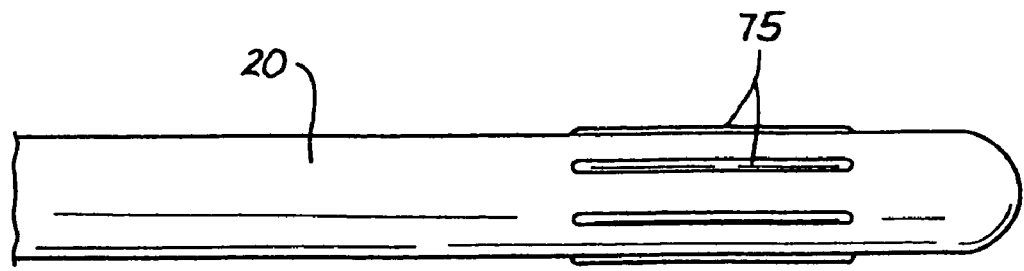
FIG. 4A depicts a catheter having longitudinal fins at the distal end of the catheter body.
Figure 4B:
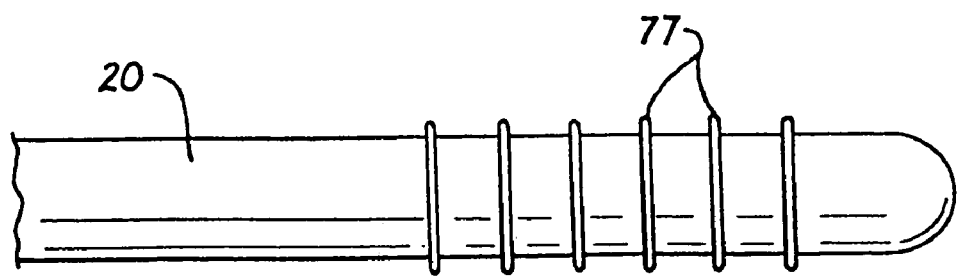
FIG. 4B depicts a catheter having radial ribs at the distal end of the catheter body.
Figure 4C:
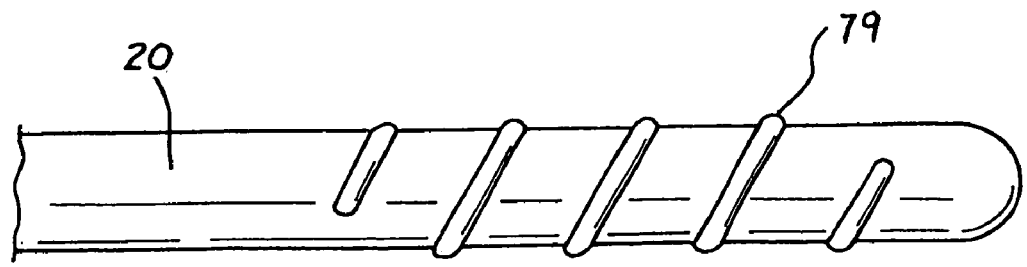
FIG. 4C depicts a catheter having a spiral fin to increase the heat transfer area at the distal end of the catheter.

FIG. 1 depicts a distal portion 15 of a heat exchange catheter 10. The catheter may be inserted through the patient's skin into a blood vessel BV. Blood flow through the vessel is indicated in FIG. 1 by a set of flow arrows F. The catheter may be inserted into a relatively large blood vessel, e.g., a femoral artery or vein, a jugular vein, since these vessels provide numerous advantages in that they are readily accessible, provide safe and convenient insertion sites, and have relatively large volumes of blood flowing through them. In general, large blood flow rates facilitate quicker heat transfer into or out of the patient. For example, the jugular vein may have a diameter of about 22 French, or a bit more than 7 millimeters (1 French=1 mm/π). A catheter suitable for insertion into a vessel of this size can be made quite large relative to catheters intended for insertion into other regions of the vascular system. Atherectomy or balloon angioplasty catheters are sometimes used to clear blockages from the coronary artery and similar vessels. These catheters commonly have external diameters in the range between 2 and 8 French. However, a catheter formed in accordance with this aspect of the invention may have an external diameter of about 10 French or more, although this dimension may obviously be varied a great deal without departing from the basic principles of the invention.

The catheter may be small enough so that the puncture site can be entered using the percutaneous Seldinger technique, a technique well known to medical practitioners. To avoid vessel trauma, the catheter will usually be less than 12 French in diameter upon insertion. Once in the vessel however, the distal or working end of the catheter can be expanded to any size so long as blood flow is not unduly impeded. Additionally, the femoral artery and vein and the jugular vein are relatively long and straight blood vessels. This will allow for the convenient insertion of a catheter having a temperature controlled region of considerable length. This is of course advantageous in that more heat may be transferred at a given temperature for a catheter of a given diameter if the length of the heat transfer region is increased. Techniques for inserting catheters into the above mentioned blood vessels are well known among medical personnel. Although the method of the present invention will probably be most commonly employed in a hospital, the procedure need not be performed in an operating room. The apparatus and procedure are so simple that the catheter may be inserted and treatment may begin in some cases even in an ambulance or in the field.

FIG. 2 depicts still another means for transferring heat to or from the distal end of a catheter. In this embodiment, catheter shaft 20 has two lumens running through it. Fluid flows from the proximal end of the catheter through in-flow lumen 60, through a heat transfer region 62, and back out through out-flow lumen 64. By supplying either warmed or cooled fluid through inflow lumen 60, heat may be transferred either to or from the patient's blood stream which flows in heat transfer proximity to the heat transfer region. The heat transfer region 62 may be in the form of a balloon 70. Use of a balloon may be advantageous in some embodiments to provide an increased surface area through which heat transfer may take place. Balloon inflation is maintained by a pressure difference in the fluid as it flows through in-flow lumen 60 and out-flow lumen 64. The balloon should be inflated to a diameter somewhat less than that of the inside diameter of the blood vessel so as not to unduly impede the flow of blood through the vessel.

FIG. 3 depicts a catheter having an internal resistance heating element 28 and a balloon 70, which is shown inflated. The balloon surface may be provided with structures that increase the surface area available for heat transfer, i.e. fins. In this embodiment, the increased surface area provided by the inflated balloon is augmented by the presence of a set of longitudinal fins 75 on the surface of the balloon. As shown in FIGS. 3 and 4A-C, longitudinal fins 75, radial ribs 77, or one or more spiral fins 79 may be disposed directly on the body 20 of a catheter. Longitudinal ribs may be advantageous because they tend to restrict blood flow through the vessel less than other configurations. In fact, these ribs insure that the balloon will not substantially block the flow of blood through the vessel because a flow path may be maintained between the ribs even when the balloon is inflated. Inclusion of a balloon on a catheter employing resistance heating allows for designs in which current is conducted through the fluid which fills the balloon.

A catheter according to the present invention may be designed and configured to optimize the rate of heat transfer between the catheter and blood flowing through the vessel. While a large surface area is desirable in order to maximize heat transfer, the catheter should be appropriately configured and sized to minimize restriction to flow through a blood vessel. Furthermore, the temperature of the catheter should be carefully controlled to prevent undesirable chemical changes within the blood. This is especially important when applying heat to the blood as blood is readily denatured by even moderately high temperatures. The exterior temperature of a catheter for warming blood should generally not exceed about 42° C.-43° C. It is estimated that a catheter whose surface temperature is controlled between 37° C. and 42° C. will provide a body core warming rate of approximately one to two degrees Celsius per hour in a patient starting out with severe hypothermia. This estimate is highly dependent on a number of factors including the rate of blood flow through the vessel, the initial body temperature of the patient, the external surface area of the catheter through which heat is conducted, etc. The actual rate achieved may vary substantially from the above estimate. The above estimate provides a starting point for a rough estimate as to the level of power transferred from the catheter to the patient's body and therefore of the size of the power supply required by the system. Regardless of the exact means of power transmission chosen, resistance heating coil, laser and diffusing tip, direct conduction or fluid circulation, an appropriate power supply will be required to provide heat to or remove heat from the system.

The sum of heat entering and leaving a patient's body can be written as:

$$\Delta H = H_c + H_i - H_e$$

where $\Delta H$ is the sum of all heat transferred, $H_c$ is the heat transferred from the catheter to the patient, $H_i$ the heat produced by the patient internally, and $H_e$ the heat lost from the patient to the environment. If one assumes, as will ordinarily be the case in a healthy patient, that the body's internal thermoregulatory system will produce just enough heat to offset heat lost to the environment, then the equation is made simple:

$$\Delta H = H_c.$$

The above equation can be written in terms of the change in the patient's internal body temperature over time as follows:

$$mc(\Delta T/\Delta t) = (\Delta H_c/\Delta t)$$

where m is the body mass of the patient, c is the specific heat of the patient's body, $(\Delta T/\Delta t)$ is the time rate of change of the patient's internal body temperature, $(\Delta H_c/\Delta t)$ is the time rate of heat delivery from the catheter to the patient. If one assumes a patient having a body mass of 75 kilograms and a specific heat of 4186 joules/° C.-kg (assumes the specific heat of the human body to be the same as that of water, the actual value will be somewhat different), then a warming rate of 1° C. per hour (3600 seconds) will require the catheter to transfer heat to the patient at a rate of about 87 watts (1 watt=1 joule/sec). However, as an estimate of the desirable size of a power supply to be used with a catheter of the present invention, this estimation may be too low. This may be true for a number of reasons. First, it was assumed for the sake of convenience that the patient's internal system would produce an amount of heat equal to that lost to the environment. In a hypothermic patient this will obviously not be the case. Almost by definition, accidental hypothermia occurs when a person's ability to produce heat internally is overwhelmed by heat lost to the environment. The catheter will have to make up the difference so the power level required will need to be greater for that reason alone. Alternatively, to induce hypothermia, sufficient heat will need to be removed from the blood to lower the temperature of the target tissue, or in the case of whole body hypothermia, to remove more heat than is generated by the body. In removal of heat, the power required to cool the heat exchanger will be largely dependent on the efficiency of the cooling device including the dissipation of excess heat from the device to the environment.

The above estimate does not allow for power losses between the power supply and whatever warming means is utilized. Such losses could include resistance losses in electrical transmission lines between the power supply and a resistance heating element, inherent inefficiencies and other losses in a system having a laser and a diffusing tip, heat losses along a thermally conductive shaft or fluid circulation lumen, and the like. Any such losses which do occur will need to be compensated for by additional power supply capacity. Furthermore, it would be undesirable to limit the performance of a catheter according to the present invention by limiting the size of the power supply used. It would be preferable instead to use a power supply capable of providing power considerably in excess of that actually needed and then controlling the delivery of that power according to the measured temperature of the catheter itself. As mentioned previously, this can be readily accomplished by including a sensitive temperature sensor within the body of the catheter. Nevertheless, the above calculation can be used as a useful estimate of the likely lower bound for sizing a power supply for use in a catheter according to the present invention.

An alternative estimate can be made by comparing the likely performance of the various embodiments described herein with the power requirements for the external blood warming apparatus presently known. Such external warming apparatus generally requires a supply of power on the order of 1000-1500 watts and sometimes more. A device formed in accordance with the present invention may require considerably less power than that. First, the present invention may not require an external pump to circulate the blood; this function is provided by the patient's own heart. Accordingly, no power is needed to drive such a pump. Secondly, the present invention may be considerably less complicated than external blood warming systems. Known systems circulate the blood over a relatively lengthy path from the patient, through the warming element, and back into the patient. More heat may be lost over this lengthy path than in devices described herein. Thus, the power required by external blood circulation and warming systems of the type previously known can be used as a rough estimate of the likely upper limit for power required by a system according to the present invention. It is most likely that such a system may be equipped with a power supply having a capacity somewhere between the two rough estimates described above. It is therefore contemplated that a suitable power supply will be capable of providing peak power somewhere in the range between 100 and 1500 watts, probably being in the range between 300 and 1000 watts. The ranges specified are an estimate of suitable peak power capability. The power supply will most commonly be thermostatically controlled in response to a temperature sensor in the body of the catheter. The actual effective power transmitted to the patient will therefore typically be much less than the peak power capacity of the system power supply.

The above calculations refer primarily to a system for heating the blood. With respect to a catheter for cooling the blood, the temperature and power constraints may not be as limiting. Care should be taken to avoid freezing the blood or inducing shock to the patient from excessively rapid cooling. The primary component of blood is essentially water with a number of suspended and dissolved substances. As such, its freezing point is somewhat below 0° C. However, a catheter adapted to cool blood in a hyperthermic patient or to induce an artificial hypothermia will usually not be operated at temperatures that low. It is presently contemplated that the external surface of such a catheter may be held in the range between about 1° C. and 20° C., although the actual temperature could vary between about 0° C. and the patient's current body temperature. Additionally, for example, of the case of a heat exchange balloon of some length, the surface temperature of the balloon may vary along its length as it gives off heat to the blood. A balloon may vary in temperature as much as 12° C. or more along its length.

Another aspect of the present invention further provides methods for both raising the body temperature of initially hypothermic patients and lowering the body temperature of patients who are initially hyperthermic, or for whom the body temperature is to be lowered below normal for some other purpose. In such cases, it is generally necessary to monitor the target tissue (which in whole body hypothermia may be the whole body and in regional may be, for example, the brain) and control the cooling so the desired temperature will not be exceeded for example, by the physiologic response of the patient. In such cases, this aspect of the invention specifically provides for reversing the heat transfer process to maintain the target tissue at the selected temperature.

Figure 5:
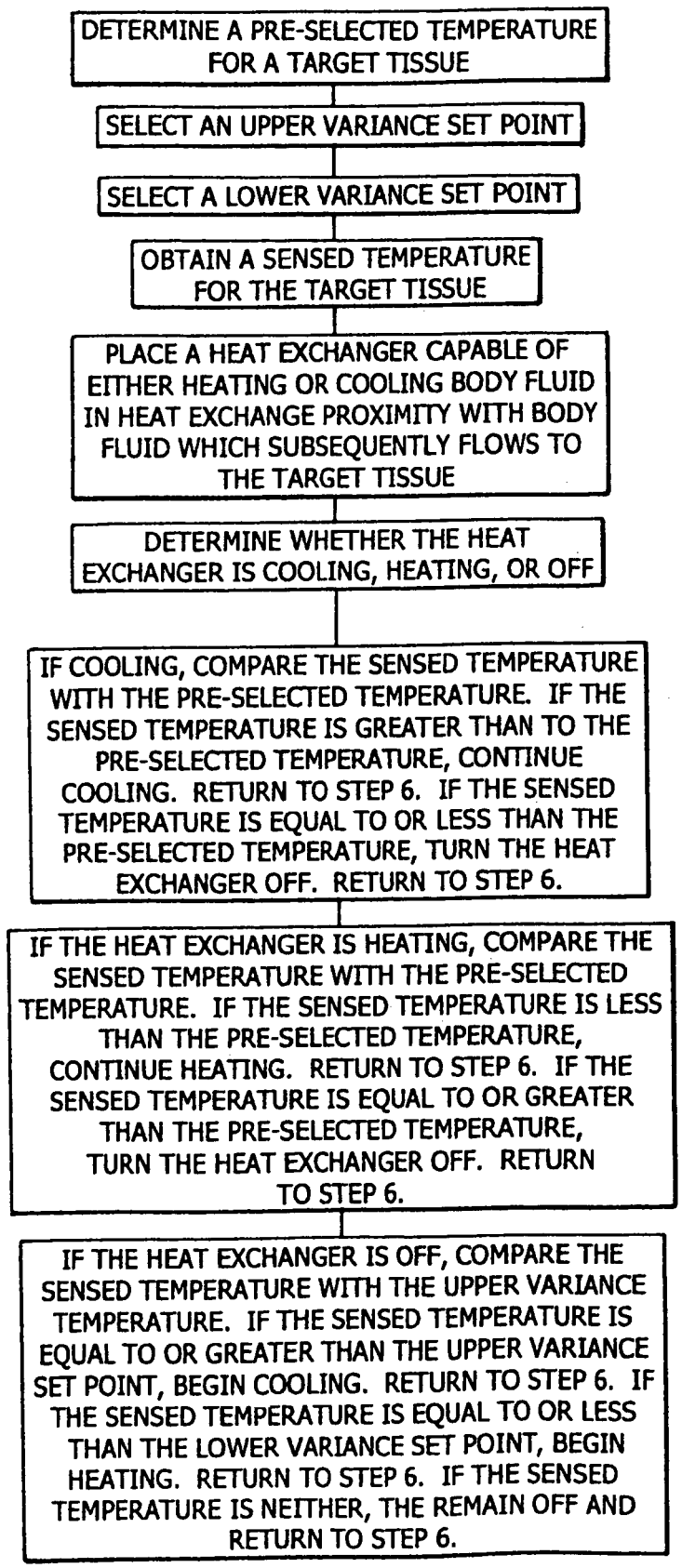
FIG. 5 is a flow chart describing the control scheme of the invention.
Figure 6:
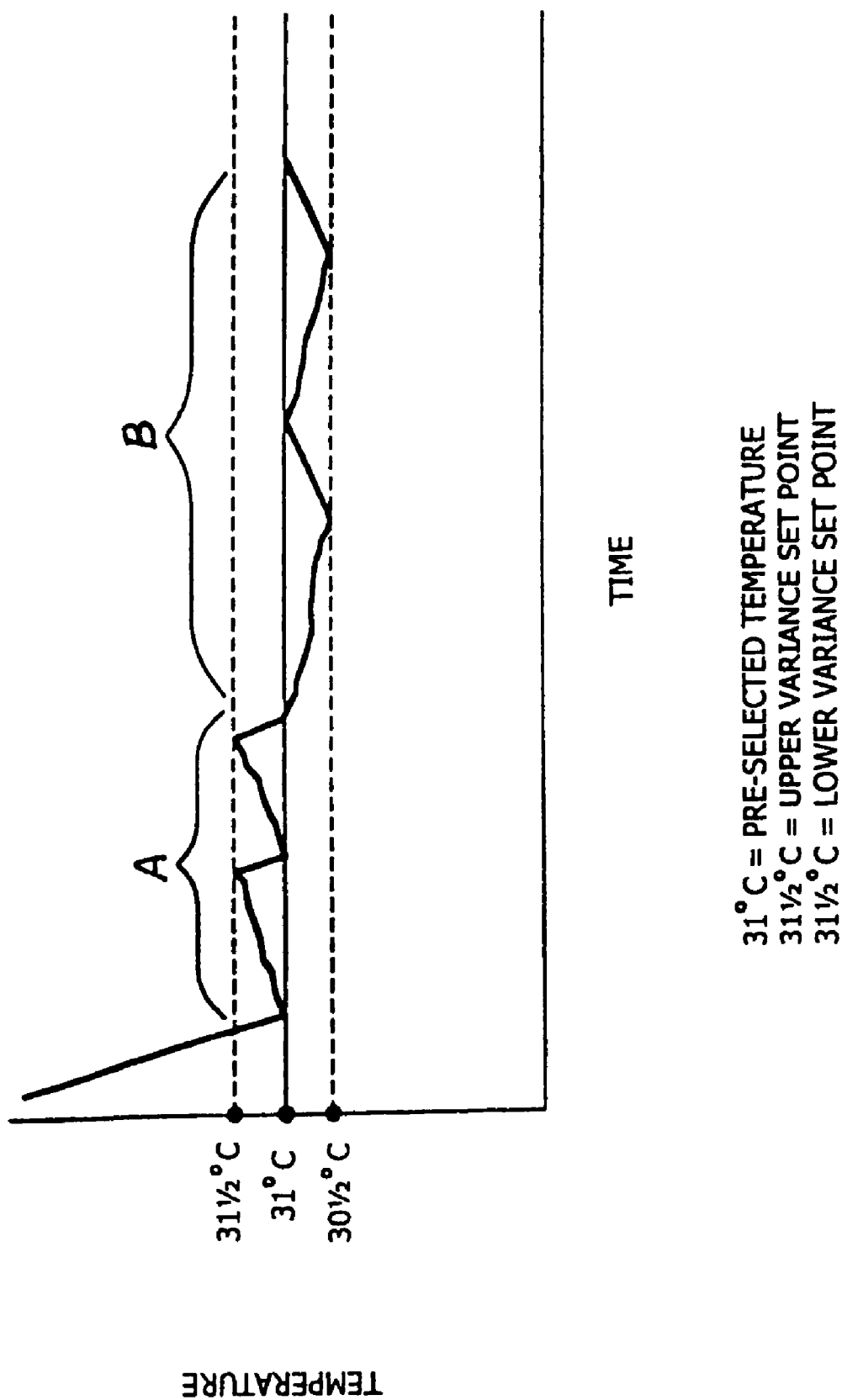
FIG. 6 is a diagrammatic representation of the temperature of target tissue under the influence of the control system of FIG. 5.

As set forth in FIG. 5, a sample control scheme is provided herein for either warming or cooling target tissue to a preferred temperature and maintaining the tissue at about the preferred temperature. The control scheme is described by the flow chart shown in FIG. 5 and illustrated with the graph shown in FIG. 6. A preferred temperature is pre-selected for the target temperature, for example a temperature of 31° C. for the brain tissue. This pre-selected temperature is communicated to a control unit, for example by setting a desired temperature on a control unit for a heat exchange catheter. A heat exchange catheter capable of either removing heat from the blood or adding heat to the blood is inserted so that it is in heat exchange proximity with blood in a blood vessel that delivers blood to a target location such as the brain. The catheter is controlled by the control unit described above that may turn the heat exchanger off or on and may control the heat exchanger to heat or cool the blood which is in heat exchange proximity with the heat exchanger.

The temperature of the brain is monitored, for example by a temperature probe inserted into the brain tissue or by measuring temperature at some proxy location such as the tympanic membrane or nasal cavity provides a temperature measurement that represents the brain temperature. This results in a sensed temperature measurement that is communicated to the controller. An upper variance set point is determined, for example ½ degree above the pre-selected temperature, and communicated to the controller. In this example, that would result in an upper variance set point of 31½°. A lower variance set point is also determined and communicated to the controller, for example ½ degree below the pre-selected temperature, resulting in this example in a lower variance set point of 30½°.

When the heat exchanger is cooling, the sensed temperature of the target tissue is compared with the pre-selected temperature. If the sensed temperature is above the pre-selected temperature, the cooling continues. If the sensed temperature falls to the pre-selected temperature or below, then the controller acts to turn the heat exchanger off. After the heat exchanger is turned off, the temperature of the target tissue is again measured to obtain a sensed temperature. If the sensed temperature is above the upper variance set point, the controller acts to cause the heat exchanger to begin cooling again. This cooling continues until the temperature again reaches the pre-selected temperature. At this point, the controller once again acts to turn the heat exchanger off. If the patient's body is generating heat in the target tissue at a rate greater than the loss to the environment, it may be seen that the temperature will oscillate between the preferred temperature and the upper variance set point, in this example, between 31° C. and 31½° C. as illustrated by section A of FIG. 6.

In some instances, the temperature of the target tissue may continue to fall spontaneously after the heat exchanger is turned off, for example if the brain tissue is giving off more heat to the environment than is generated by the brain. In such a situation the sensed temperature may continue to fall until it is below the lower variance set point. If it does, the controller acts to cause the heat exchanger to add heat to the blood and thus to the target tissue until the sensed temperature is again at the pre-selected temperature. The controller then turns the heat exchange catheter off. If the temperature again falls until it reaches a temperature below the lower variance set point, the process is repeated. If this situation repeats, it may be seen that the temperature will oscillate between the pre-selected temperature and the lower variance set point, in this example, between 31° C. and 30½° C. as illustrated by section B of FIG. 6.

The example given here was for purposes of illustration only and many variations will be anticipated within the scope of this invention. For example, the pre-selected temperature and upper and lower variance set points may be different than those described above. The discussion above was an example of cooling the target tissue to a temperature below normothermic. However it may be seen that a pre-selected temperature above normothermic may also be selected, and a heat exchanger which is controlled to both add heat to the blood or remove heat from the blood may, through use of the same control scheme, maintain the temperature of the target tissue at the preferred temperature within the upper and lower variance set points around a pre-selected temperature above normothermic. It may also be readily perceived that a patient that is hypothermic may be rewarmed to normothermia by setting the preselected temperature in the control scheme illustrated to 37° which will cause the heating element to warm the blood until the sensed temperature reaches 37°. The anticipation and prevention of temperature overshoot may be accomplished as described in U.S. patent application Ser. No. 08/584,013 previously incorporated herein by reference.

In the example given, the steps are all stated as discrete actions, such as measuring the temperature of the target tissue or comparing sensed and pre-selected temperatures, but it may be readily understood by one of skill in the art that the actions may be relatively continuous. It will also be readily appreciated that control criteria other than the temperature of the target tissue may be substituted and controlled, for example blood pressure or cranial pressure, or temperature derived from some other location, and two control schemes as described may be simultaneously instituted for different locations in the patient, for example, to cool a region such as the brain and maintain that region in a relatively stable cooled condition while simultaneously warming the core temperature of the patient to normothermic and maintaining the patient's core temperature relatively stable at a normothermic temperature. The method of affecting the target tissue's temperature discussed above was cooling the blood upstream from the target tissue, but it may be appreciated that other methods of heating and cooling, for example heating or cooling cerebrospinal fluid circulating around the brain or spinal cord may be employed.

Figure 7:
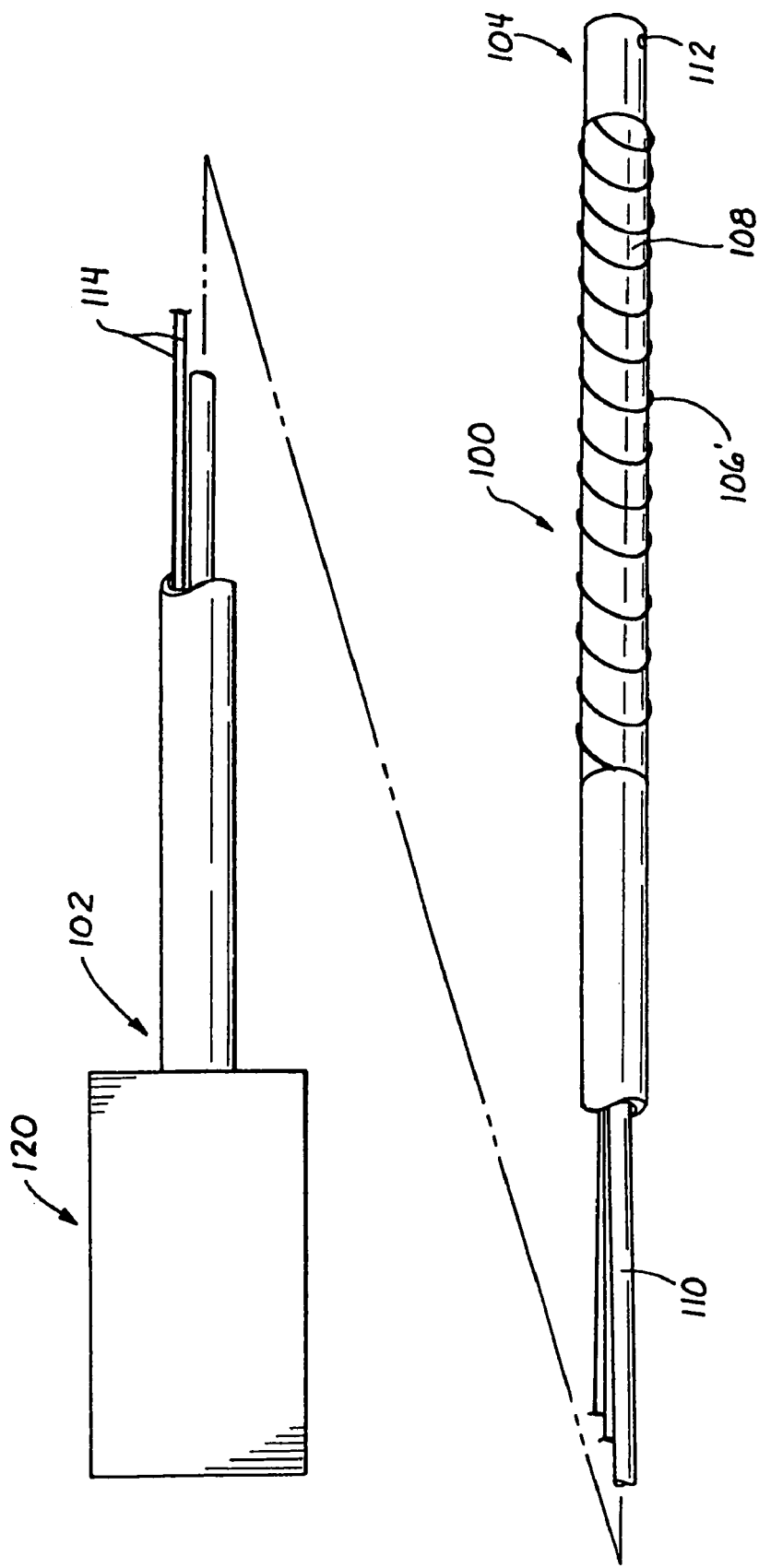
FIG. 7 illustrates a preferred catheter for the selective heating and cooling of patient blood flow employing a wire coil resistance heater and a metal foil cooling element.

A system for the selective warming and cooling of patients is illustrated in FIG. 7. The system may comprise a catheter 100 having a proximal end 102, a distal end 104, a heat-generating surface 106 near the distal end, and a heat-absorbing surface near the distal end 108. The heat-generating surface 106 may include any of the heat transfer components described above, particularly a wire coil resistance heater as shown having from 50 to 1000 windings, typically spaced-apart from 0.1 mm to 1 mm. The total length of the catheter may range from 15 cm to 50 cm, and may measure from about 1 mm to 5 mm in diameter. The windings may extend over a total distance in the range from 10 cm to 20 cm near the distal end. The heat-absorbing surface may be a thermally conductive metal foil, typically composed of a biologically compatible thermally conductive metal, such as gold, silver, aluminum, or the like. Copper may also be useful, but should be treated or encapsulated in order to enhance its biocompatibility. The metal foil may be thin in order to enhance flexibility of the catheter body, typically having a thickness in the range from 0.001 mm to 0.01 mm. The heat-absorbing surface 108 may be conductively coupled to a cooler located externally of the catheter, typically in a control unit 120 as described below. In the illustrated embodiment, the surface 108 is coupled by a thermally conductive core member 110 composed of a flexible rod or wire formed from one of the thermally conductive metals described above. Alternatively, thermal coupling can be achieved by extending the surface 108 proximally so that the proximal end of the surface can be coupled to the cooler. In the latter case, it may be preferable that the proximal portions of the surface 108 be thermally insulated to prevent cooling outside of the blood circulation. The system may further comprise a control unit 120 which typically provides both the heat-generator and the cooler for coupling to the catheter 100. The heat-generator may also comprise a direct current source for coupling to the resistance heater on the catheter. Usually, the direct current source will be a commercially available, temperature-controlled DC power supply, typically operating at a voltage in the range from 10 VDC to 60 VDC and a current output in the range from 1 A to 2.5 A. The power supply may be controlled to maintain the surface temperature of the heating surface 106 in the range from 40° C. to 42° C. As discussed above, the surface temperature should not exceed 42° C. in order to prevent damage to blood components. Other desirable characteristics of the heat exchange surface are described above.

Alternatively, the temperature of the heat exchange surface can also be controlled based on measured blood temperature and/or measured body temperature. Blood temperature can be measured by temperature sensors present on the catheter. For example, a temperature sensor 112 may be located on the catheter spaced-apart from the heat exchange surfaces 106 and 108. The temperature sensor 112 may be located either upstream or downstream from the heat exchange surfaces based on the direction of blood flow and depending on the manner in which the catheter is introduced to the patient. Optionally, a pair of temperature sensors could be provided, one disposed on each side of the heat exchange surfaces in order to measure both upstream and downstream blood temperatures. The catheter may also include a temperature sensor (not shown) coupled directly to the heat-generating surface 106 so that the temperature of the surface may be directly controlled. Other temperature sensors (not shown) may be provided for directly measuring the patient's core body temperature or the temperature of various regions of the patient's body, with the temperatures being fed back into the control unit 120. The cooler in control unit 120 may be any type of refrigeration unit capable of removing heat from the heat-absorbing surface 106 at a rate sufficient to cool the blood at a desired rate. Typically, the cooler may be rated at from 150 W to 350 W.

The cooler will be a thermoelectric cooler, such as those commercially available from Melcor Thermoelectrics, Trenton, N.J. 08648. The cooler may be directly coupled to the core element 110 so that direct heat conduction from the heat-absorbing surface 108 may be effected to the cooler in control unit 120. The temperature of the cooling surface 108 may be less critical than that of the heating surface 106 with regard to this aspect of the invention, but will usually be maintained in the range from 0° C. to 35° C. preferably being below 30° C. The temperature of the cooling surface may be directly controlled within this range, or alternatively, the system may be designed so that the cooling temperature operates approximately within this range based on the total system characteristics.

The control unit 120 may further include one or more temperature controllers for controlling the temperature of the heat-generating surface 106 and the heat-absorbing surface 106 based on the blood temperature and/or the body temperature. At a minimum, the control unit 120 may control the temperature of the heat-generating surface 106 within the range set forth above, and may monitor at least one of the patient blood temperature and patient body temperature in order to reverse the heating or cooling mode as discussed above. With respect to the control scheme described in FIG. 10, for example, the system may operate in an on-off mode where for example hypothermic patients are initially treated by warming the blood at a constant surface temperature rate until a target temperature is reached. When the target temperature is reached, power to the heat-generating surface 106 is turned off. Monitoring of the blood and/or patient body temperature, however, is maintained to assure that the patient temperature does not exceed a maximum which is above the target temperature. Should the maximum be exceeded, then the system is operated in the cooling mode until the excess body temperature is lowered. Usually, there will be no need to again warm the patient, but the present system may provide for further cycles of warming and cooling if necessary. For initially hyperthermic patients, the cooling and warming modes are reversed. It will be appreciated that the temperature control schemes of the present invention could be substantially more sophisticated. For example, the power input to warm the patient could be controlled based on proportional, derivative, or integral control schemes which will typically provide for a tapering of the heat transfer rate as the patient's core or regional body temperature approaches the desired target level. Moreover, cascade control schemes based on both patient blood temperature and patient body temperature could be devised. Such control schemes, for example, could be adapted both for warming the patient and cooling the patient with mathematical models of typical patient physiological characteristics being taken into account in preparing the control schemes. However, a simple off-on control scheme that is capable of reversing the heat transfer mode if the target temperature is exceeded by more than a safe amount will be sufficient.

Another aspect of the invention provides methods and apparatus for regulating the temperature of a fluid that is to be delivered to a target location within a patient while the fluid is within the body. The regulation of the fluid temperature in this manner lends itself to a variety of applications including heating or cooling the temperature of drugs, solutes, or blood before their delivery to a target site. Regulation of the temperature of the injected fluid may also find use in regulating the temperature of the target location itself in preparation for various medical procedures, including neurosurgical procedures within the brain. Further, the methods and apparatus allow for the temperature of tissue within a patient's body temperature to be controlled by warming or cooling the patient's blood in situ. By warming or cooling the patient's blood that subsequently flows to that tissue, the temperature of the tissue in question may thereby be increased or decreased as desired. Such methods and apparatus therefore provide a convenient therapy for treating hypothermia or hyperthermia, or for inducing regional cooling or heating.

Figure 8:
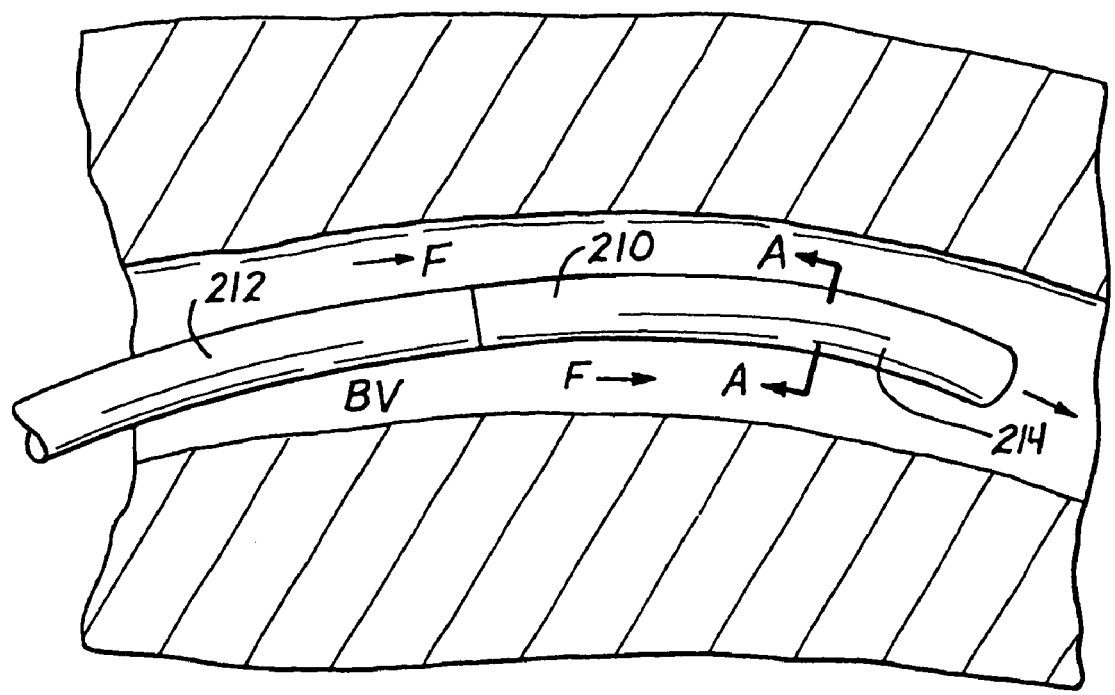
FIG. 8 depicts a distal end of a catheter according to the present invention which is inserted into a vessel of a patient.
Figure 8A:
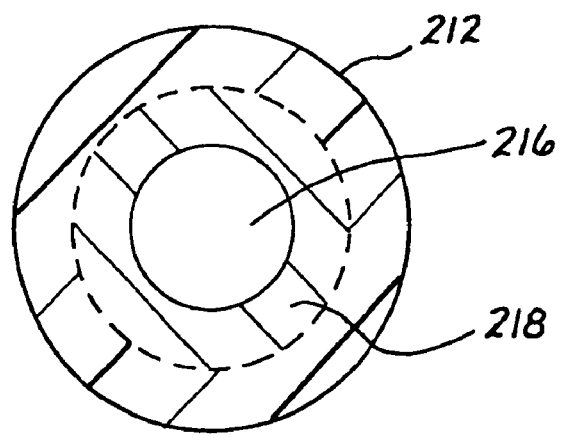
FIG. 8A is a cross-sectional side view of a catheter shown in FIG. 8 taken along lines A-A and depicting a temperature altering region.

FIG. 8 depicts a distal end 210 of a catheter 212 formed in accordance with another aspect of the present invention. The catheter 212 may be positioned within a blood vessel BV. Blood flow through the vessel is indicated in FIG. 8 by a set of arrows F. The distal end 210 of the catheter 212 may include a temperature altering region 214 although it will be appreciated that the temperature altering region may be located anywhere between the proximal and the distal catheter end. Techniques for inserting catheters into various blood vessels such as the Seldinger technique mentioned above, are well known among medical personnel. The catheter 212 may be manufactured in various sizes depending upon the particular application. For most uses, it may have a length in the range from about 30 cm to about 130 cm, and a diameter in the range from 6 to 12 French (1 French=0.33 mm). The catheter 212 will preferably be flexible to allow the catheter to be moved through various vessels within a patient, and may be positioned in the body preferably with the assistance of a guidewire.

Figure 9:
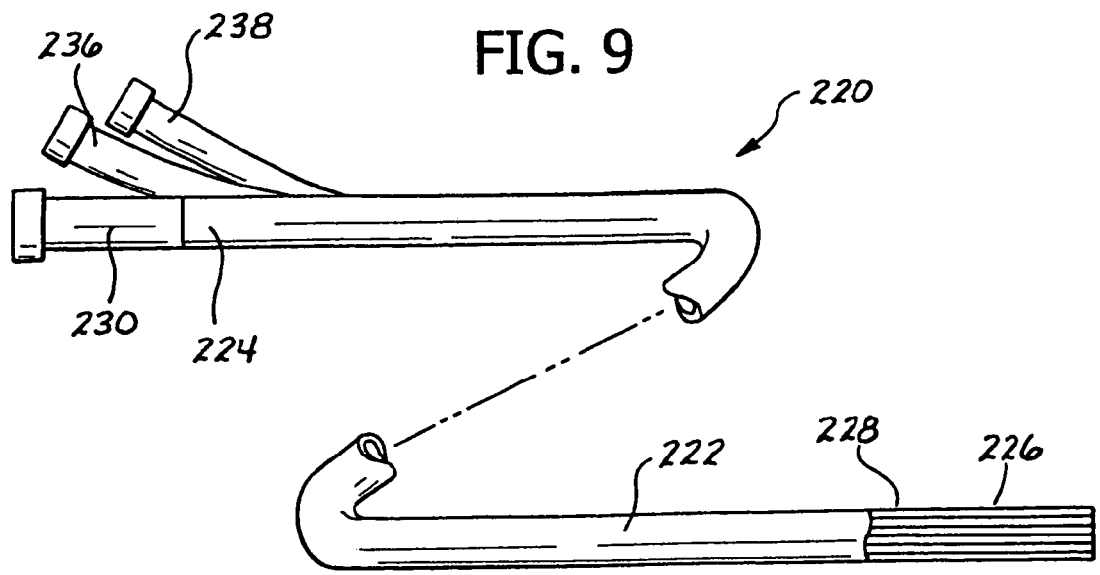
FIG. 9 is a side view of an exemplary catheter for heating or cooling a fluid passing through an internal lumen according to the invention.

As shown in FIG. 9, the catheter 212 may include an internal lumen 216. A temperature altering mechanism 218 may be provided adjacent the luminal wall of the lumen 216 at the temperature altering region 214. For convenience of discussion, the temperature altering mechanism 218 is illustrated schematically and may comprise a variety of mechanisms that are employed to either heat or cool the luminal wall of the lumen 216 to heat or cool the fluid passing through the lumen 216 at the temperature altering region 214. Exemplary mechanisms for heating or cooling the luminal wall may include heated or cooled fluids passing through the catheter 212 near the luminal wall, resistive elements disposed within the catheter 212, laser energy that is supplied to the temperature altering region, various chemicals disposed within the catheter body, thermoelectric crystal, and the like. Use of such mechanisms allow fluids passing through the lumen 216 at the temperature altering region 214 to have their temperature altered so that they will be within a desired range when exiting the catheter 212. The temperature altering mechanism 218 may be configured to heat a fluid passing through the temperature altering region so that its temperature will be heated by at least 5° C. to about 42° C. When cooling a fluid, the temperature altering mechanism 218 may be configured to cool the fluid by at least 7° C. to about 30° C. The temperature altering mechanism 218 may be designed to optimize the rate of heat transfer between the catheter and a fluid flowing through the internal lumen. Further, the temperature of the catheter may be carefully controlled to prevent undesirable chemical changes within the blood. This is especially important when applying heat to the blood as blood is readily denatured by even moderately high temperatures. The temperature of the luminal wall for warming blood should generally not exceed about 42° C. to 43° C. The amount of energy that may be supplied to heat a patient's core body temperature is described in U.S. Pat. No. 5,486,208, previously incorporated by reference herein. The temperature altering mechanism 218 may be also arranged within the catheter 212 so that the temperature of the luminal wall may be heated or cooled without substantial direct heating of an outer surface of the catheter. In this way, the catheter 212 may be employed to selectively heat or cool a specific target site by simply positioning the distal end of the catheter at the target site and introducing a fluid through the lumen 216.

Figure 10:
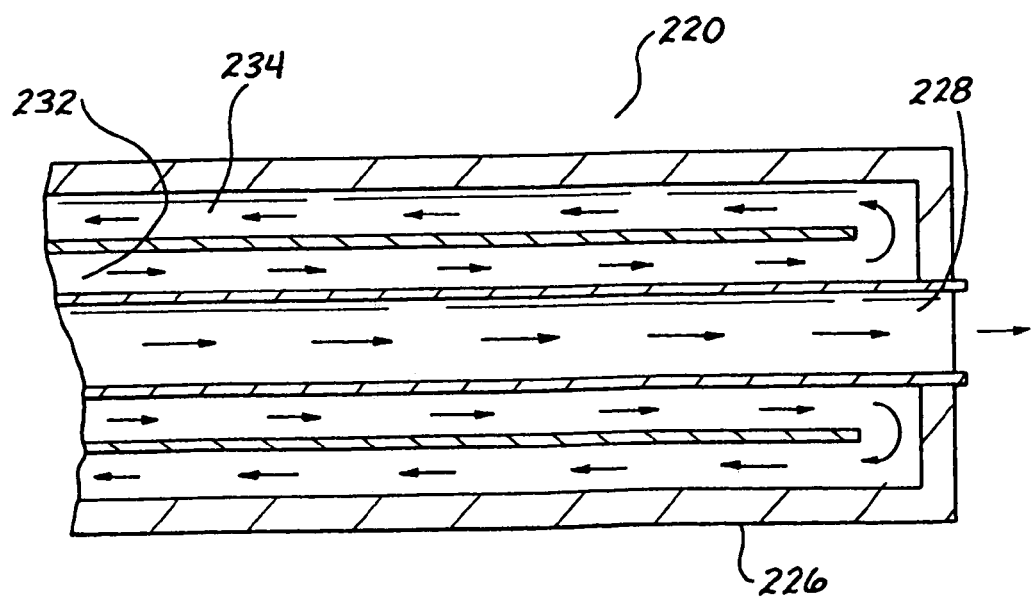
FIG. 10 is a more detailed view of a distal end of a catheter similarly shown in FIG. 9.

As shown in FIGS. 9 and 10, a catheter 220 formed in accordance with this aspect of the invention may circulate a heat transfer fluid to alter the temperature of a fluid passing through the catheter. The catheter 220 comprises a catheter body 222 having a proximal end 224 and a distal end 226. A lumen 228 extends between the proximal end 224 and the distal end 226. At the proximal end 224, is a proximal port 230 through which various fluids may be introduced into the lumen 228 from outside of a patient. Passing through the catheter body 222 is a first fluid path 232 and a second fluid path 234 as particularly shown in FIG. 10. A first port 236 is in communication with the first fluid path 232 and a second port 238 is in communication with the second fluid path 234. In this manner, a heated or cooled heat transfer fluid may be introduced into the first port 236 where it passes through the first fluid path 232 adjacent to the lumen 228. As the heat transfer fluid passes through the first fluid path 232, heat is transferred either to or from a fluid passing through the lumen 228 to heat or cool the fluid to a desired temperature before exiting the catheter body 222. After passing through the first fluid path 232, the heat transfer fluid circulates back through catheter body 222 through the second fluid path 234 where it exits the second port 238.

FIGS. 11 and 11A provide illustrations of yet another variation of the invention that includes a catheter 240 with resistive heating to heat a fluid passing through the catheter. The catheter 240 comprises a catheter body 242 having a proximal end 244 and a distal end 246. A lumen 248 passes through the catheter body 242 between its proximal end 244 and distal end 246. A proximal port 250 is provided to facilitate the introduction of fluids into the lumen 248 from outside a patient. Disposed within the catheter body 242 near the lumen 248 are a plurality of wires 252 as shown in FIG. 17. These wires 252 may exit the catheter body 242 through a port 254. The wires 252 may be also connected to either a DC or low frequency AC power supply. As electrical current passes through the wires 252, some of the energy is dissipated as heat to heat the luminal wall. Alternatively, a radio frequency or RF power supply may be employed to supply power to electrodes disposed within the catheter body 242 to heat the luminal wall.

Referring now to FIGS. 12-14, a catheter 256 may be employed to heat or cool an externally injected fluid, to heat or cool a body fluid in situ, or a combination of both. The catheter 256 may comprise a catheter body 258 having a proximal end 260 and a distal end 262. Extending between the proximal end 260 and the distal end 262 is a lumen 264 as shown in FIG. 12. A proximal port 266 is also provided at the proximal end 260 to allow various fluids to be injected into the lumen 264 while port 266 is positioned outside a patient. At the distal end 262 is a temperature altering region 268 which includes a temperature altering mechanism (not shown). The particular temperature altering mechanism may comprise any of those described with respect to other aspects of the invention set forth above or hereafter. In this manner, a fluid which is injected into the port 266 will pass through the lumen 264 and have its temperature altered when passing through the temperature altering region 268 in a manner similar to that previously described with other embodiments. The catheter body 258 may include a plurality of perfusion orifices 270 which extend through the wall of the catheter body to provide fluid paths to the lumen 264. As shown by the arrows in FIG. 12, a body fluid, such as blood, may pass through the orifices 270 and into the lumen 264 where it will have its temperature altered at the temperature altering region 268 so that the temperature of the body fluid will be within a desired range when exiting the catheter body 258 at its distal end 262 as shown.

As illustrated in FIGS. 13 and 14, the luminal wall of the catheter body 258 may include a plurality of flaps 272. These flaps 272 may control the passage of body fluids through the orifices 270 and into the lumen 264. These flaps 272 or similar structures may be also constructed as described in U.S. Pat. No. 5,180,364, the disclosure of which is herein incorporated by reference. When a fluid is injected into the lumen 264 at the port 266, the pressure and direction of flow of the injected fluid will cause the flaps 272 to close over the orifices 270 as shown in FIG. 13 so that essentially only the injected fluid will pass through the temperature altering region 268. In this way, the temperature of the injected fluid will have its temperature altered so that it will be within a desired range when exiting the distal end. As shown in FIG. 14, when no fluids are injected into the port 266, the pressure of the body fluid within a vessel will cause the flaps 272 to open to allow the body fluids to flow through the orifices 270 and into the lumen 264. In this manner, a body fluid, such as blood, may have its temperature altered by passing through the orifices 270 and through the temperature altering region 268. The configuration of the flaps 272 is particularly advantageous in applications where the temperature of a patient's tissue is altered. By simply introducing the catheter 256 into the patient, the blood which flows into the lumen 264 via the orifices 270 will have its temperature altered by the time it exits the distal end 262. This may result in whole body temperature alteration, or if the blood is directed to a specific site by the catheter, may result in regional temperature alteration. In the event that a solute or drug is also needed for therapy, it may be introduced into the lumen 264 through the port 266 and have its temperature be substantially the same as the exiting blood temperature. As described above, this aspect of the invention provides methods and apparatus which are useful in regulating the temperature of various fluids while such fluids are within a patient. With such an arrangement, a variety of procedures may be performed including the introduction of a drug or solute from outside the patient that may have its temperature altered within the catheter before reaching a target location. Furthermore, a fluid may be heated or cooled within the catheter to in turn heat or cool a specific region of a body structure prior to the performance of a medical procedure. In another alternative, the temperature of a patient's body fluid, such as blood, may be altered in situ to treat a patient suffering from either hypothermia or hyperthermia, or to intentionally induce either whole body or regional hypothermia.

Another aspect of the present invention provides methods and apparatus for regional and whole body temperature modification. The lowering of body temperature for selected regions may provide a neuroprotective effect particularly in proximity to the brain. Selected portions of at least one catheter may, for example, cool fluids such as blood or cerebral spinal fluid that are in contact with, circulating in, around, or leading to the brain region. The cooled body fluid may be selectively directed to a chosen region of the patient's body for producing a regionally confined cooling effect. Alternatively, a patient's whole body temperature may be reduced to provide, for example, neuroprotection for the entire brain and other widely spaced tissue such as the spinal cord. As will be discussed in further detail below, methods and apparatus provided herein may include a heat exchange catheter formed with an increased surface area or a finned section to provide rapid and effective heat transfer. A regionally confined thermal transfer region along a catheter body having a longitudinal dimension may further provide effective heat transfer with fluids traveling within an inner passageway, while the catheter may further provide a zone of regional cooling or heat transfer along selected portions of the catheter. Various combinations of both heating and cooling elements may be defined along different portions of a single catheter, or as part of a series or combination of heat exchange devices as similarly described with respect to other aspects of the invention. All of these devices and procedures may be directed to regional or selected body temperature modification that is particularly suitable for the cooling of the cerebral region, and for inducing an artificial state of hypothermia that may provide therapeutic benefits in the treatment of cerebrovascular injury. The system may be a simple heat transfer catheter with manual controls, or may be operated by means of a controller that may monitor a number of sensors and control the heat exchange catheter in response to data received form said sensors.

Figure 15:
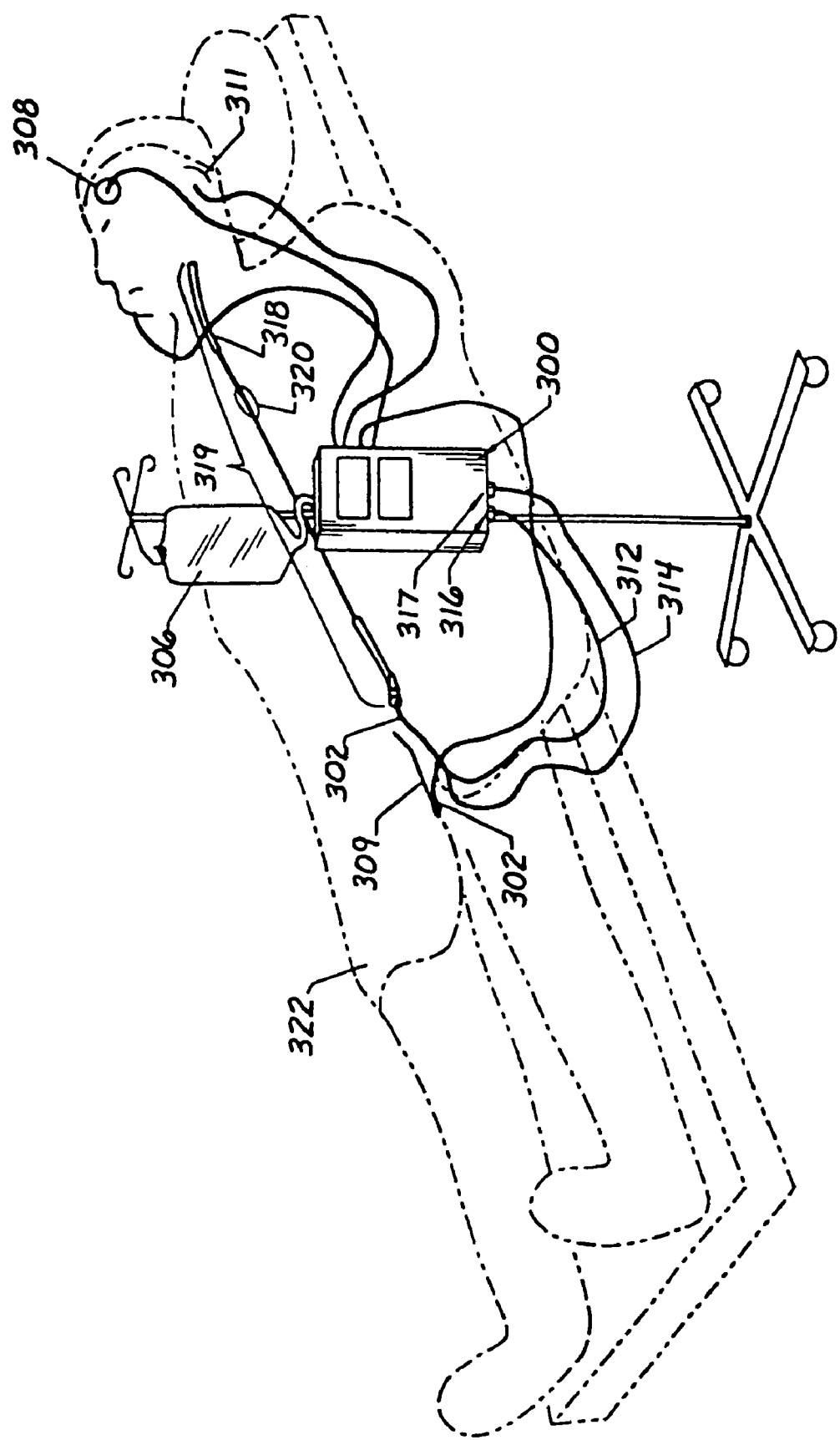
FIG. 15 is a perspective view of a heat transfer catheter system connected to a patient that may include monitoring devices, a controller, and a thermal catheter with multiple heat transfer portions.

As generally shown in FIG. 15, a heat transfer catheter system directed to this aspect of the invention may include a catheter control unit 300 and a heat transfer catheter 302 formed with a combination of at least one heat transfer section. The heat transfer section or sections are located on that portion of the catheter, as illustrated by section 319, that is inserted into the patient. This insertion portion is less than the full length of the catheter and extends from the location on the catheter just inside the patient, when the catheter is fully inserted, to the distal end of the catheter. The catheter control unit 300 may include a fluid pump for circulating a heat exchange fluid or medium within the catheter 302, and a combination of at least one heat exchanger component for heating and/or cooling circulating fluids within the heat transfer system. A reservoir or fluid bag 306 may be connected to the control unit 300 to provide a source of heat transfer fluid such as, saline, blood substitute solution or other biocompatible fluid. The control unit 300 may further receive data from a variety of sensors which may be, for example, solid state thermocouples to provide feedback and patient temperature information from selected organs or portions of the body such as a temperature probes for the brain and head region 308, a rectal temperature probe 309, an ear temperature probe 311, a bladder temperature probe (not shown) and the like. Based upon sensed temperatures and conditions, the control unit 300 may direct the heating or cooling of the catheter in response to input from the sensors. The control unit 300 may activate a heat exchanger at a first sensed temperature, and may also deactivate the heat exchanger at a second sensed temperature which may be relatively higher or lower than the first sensed temperature or any other predetermined temperature. The control unit 300 may of course independently heat or cool selected heat transfer sections to attain desired or preselected temperatures in body regions. Likewise the controller may activate more than one heat exchanger to control temperature at particular regions of the patient's body. The controller might also activate or deactivate other apparatus, for example, external heating blankets or the like, in response to sensed temperatures. The controller may function as described above and illustrated in FIGS. 5 and 6.

The temperature regulating catheter 302 illustrated in FIG. 15 may also provide various zones of cooling and/or heating by circulating heat transfer medium through a series of inlet and an outlet conduits. A first and a second fluid path 312 and 314 may provide a heat exchanger channel within the catheter, and may be respectively connected to the inlet 316 and outlet 317 of a pump for circulation of a heat transfer fluid to cool the flow of fluid within a selected body region. A similar arrangement may be implemented for heating a selected body region simultaneously or independently from the cooling component of the system. The catheter control unit 300 may further include a thermoelectric cooler and heater which are selectively activated and deactivated to perform both heating and cooling functions with the same or different heat transfer medium within the closed-loop catheter system. For example, a first heat transfer section 318 of at least one temperature regulating catheter 302 and located on the insertion portion 319 of that catheter, may circulate a cold solution in the immediate head region, or alternatively, within a carotid artery or other blood vessel leading to the brain. The head temperature may be locally monitored with temperature sensors 308 positioned on a relatively proximate exterior surface of the patient or within selected body regions. Another or a second heat transfer section 320 of the catheter 302, also located on the insertion portion 319, may circulate a heated solution within a collapsible balloon or otherwise provide heat to other body locations through heating elements other mechanisms described in accordance with other aspects of the invention. While the heat transfer catheter 302 may provide regional hypothermia to the brain region for neuroprotective benefits, other parts of the body may be kept relatively warm so that adverse side effects such as shivering may be avoided or minimized. Warming of the body generally below the neck may be further achieved by insulating or wrapping the relatively lower body in a heating pad or blanket 322 while the head region 310 above the neck is cooled. It should be understood of course that multiple heat transfer sections of the catheter 302 may be modified to provide whole body cooling or warming to affect body core temperature, and is not just limited to regional or localized body temperature regulation.

Figure 16:
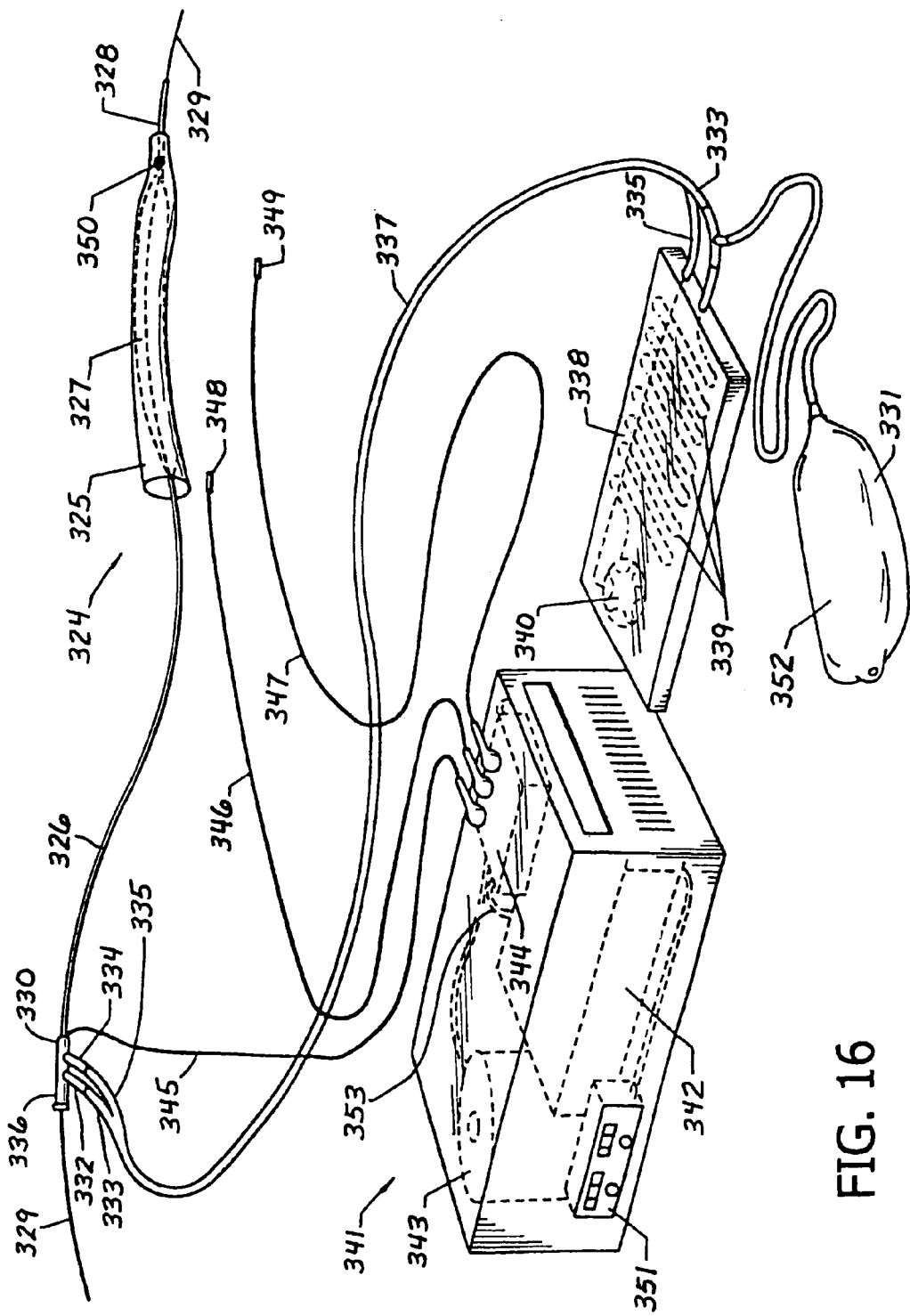
FIG. 16 is a simplified perspective view of a heat transfer catheter system with a controller, disposable components, reusable components, a heat exchange balloon catheter and various sensors.

FIG. 16 provides an illustration of the heat transfer catheter system of the invention which includes disposable components including a heat transfer catheter 324, a disposable heat exchange plate 338, a pump head assembly 340, a saline bag 339, sensors 348, 344 and a fluid flow line 337, as well as reusable components including a solid state thermoelectric heater/cooler 342, a pump driver 343 and various controls for the unit.

The heat transfer catheter 324 is formed with a blood channeling sleeve 325, a catheter shaft 326, and a heat exchanger 327 which may be for example a heat exchange balloon operated using closed-loop flow of heat exchange medium. The catheter shaft may be formed with a working lumen 328 for injection of drugs, fluoroscopic dye, or the like, and for receipt of a guide wire 329 for use in placing the heat transfer catheter at an appropriate location in the patient's body. The proximal end of the shaft may be connected to a multi-arm adapter 330 for providing separate access to various channels in the catheter shaft. For example, one arm 336 may provide access to the central lumen 328 of the catheter shaft for insertion of a guide wire 329 to steer the heat transfer catheter to the desired location. Where the heat exchanger 327 is a heat exchange balloon for closed-loop flow of a heat exchange medium 331, the adapter may contain an arm 332 to connect an inlet flow line 333 to an inlet flow channel (not shown in this Fig.) within the catheter shaft, a separate arm 334 to connect an outlet fluid line 335 to an outlet flow channel (also not shown in this Fig.) A dual channel flow line 337 may contain both inlet and outlet flow lines 333, 335 to connect the catheter shaft 326 to a disposable heat exchange plate 338. Additionally, one of the flow lines, for example the inlet flow line 333 may be connected to a bag 339 of heat exchange fluid 331 to prime the closed-loop heat exchange balloon catheter system as necessary.

The heat exchange plate 338 may include a serpentine pathway 339 for the heat exchange fluid to be pumped through the heat exchange plate by means of a disposable pump head 340. The heat exchange plate including the serpentine pathway and the pump head is configured to install into a reusable master control unit 341. The master control unit may include a heat generating or removing unit 342 such as a thermoelectric heater/cooler (TE cooler). A TE cooler is particularly advantageous because the same unit is capable of either generating heat or removing heat by changing the polarity of current activating the unit. Therefore it may be conveniently controlled to supply or remove heat from the system without the need of two separate units.

The master control unit includes a pump drive 343 that activates the pump head 340 to pump the heat exchange fluid 331 and cause it to circulate through the heat exchanger 327 and the serpentine path in the heat exchange plate. When installed, the heat exchange plate is in thermal communication with the TE cooler, and thus the TE cooler may act to heat or cool the heat exchange fluid as that fluid is circulated through the serpentine pathway. When the heat exchange fluid is circulated through the heat exchanger located in a patient's body, it may act to add or remove heat from the body. In this way the TE cooler may act to affect the blood temperature of a patient as desired.

The TE cooler and the pump are responsive to a controller unit 344. The control unit receives data input through electrical connections 345, 346, 347 to numerous sensors, for example body temperature sensors 348, 349 that may sense temperatures from a patient's ear, brain region, bladder, rectum, esophagus or other appropriate location as desired by the operator who places the sensors. Likewise, a sensor 350 may monitor the temperature of the heat exchange balloon, and other sensors (not shown) may be provided as desired to monitor the blood temperature at the distal tip of the catheter, at the proximal tip of the catheter, or other desired location.

An operator by means of the manual input unit 351 may provide the operating parameters of the control system, for example a pre-selected temperature for the brain. The parameters are communicated to the control unit 344 by means of a connection 353 between the manual input unit and the control unit.

In practice, the operator using the manual input unit supplies a set of parameters to the control unit 344. For example, a desired temperature for the brain region and/or the whole body of the patient may be specified as the pre-selected temperature. Data is received from the sensors 348, 349 indicating for example, a sensed temperature of the patient at the location of the sensors, e.g. the actual core body temperature of the patient or the actual temperature of the brain region. Other data input may include the actual temperature of the heat exchanger, the temperature of blood at the distal end of the catheter body, or the like.

The control unit coordinates the data and selectively actuates the various units of the system to achieve and maintain parameters. For example, it may actuate the TE cooler to increase the amount of heat it is removing if the actual temperature is above the specified temperature, or decreasing the amount of heat being removed if the temperature is below the specified temperature. It may stop the pumping of the heat exchange fluid when the body or regional temperature sensed is the desired temperature.

The controller may have a buffer range for operation wherein a target temperature is established, and an upper variance set point temperature and lower variance set point temperature are also set. In this way, the controller may cause the heat exchanger to operate until the target temperature is reached. At that temperature, the controller may suspend the operation of the heat exchanger until either the upper variance set point temperature is sensed or the lower variance set point temperature is reached. When the upper variance set point temperature is sensed, the controller would then activate the heat exchanger to remove heat from the blood stream. On the other hand, if the lower variance set point temperature is sensed, then the controller would activate the heat exchanger to add heat to the blood stream. This control scheme is similar to that illustrated in FIGS. 5 and 6 discussed above. Such a control scheme as applied to this system has the advantage of allowing the operator to essentially dial in a desired temperature and the system will act to reach that target temperature and maintain the patient at that target temperature. At the same time, a buffer range is established so that when the target temperature is reached, the controller will generally not turn the TE cooler on and off or activate and deactivate the pump drive in rapid succession, actions that would be potentially damaging to the electric units in question.

It may also be perceived, in keeping with the present invention, that the controller may be configured to simultaneously respond to several sensors, or to activate or deactivate various components such as several heat exchangers. In this way, for example, a controller might heat blood that is subsequently circulated to the core body in response to a sensed core body temperature that is below the target temperature, and simultaneously activate a second heat exchanger to cool blood that is directed to the brain region in response to a sensed brain temperature that is above the target temperature. It may be that the sensed body temperature is at the target temperature and thus the heat exchanger that is in contact with blood circulating to the core body may be turned off by the controller, while at the same time the controller continues to activate the heat exchanger to cool blood that is directed to the brain region. Any of the many control schemes that may be anticipated by an operator and programmed into the control unit are contemplated by this invention.

An advantage of the system as illustrated is that all the portions of the system that are in contact with the patient are disposable, but substantial and relatively expensive portions of the system are reusable. Thus the catheter, the flow path for sterile heat exchange fluid, the sterile heat exchange fluid itself, and the pump head are all disposable. Even if a rupture in the heat exchange balloon permits the heat exchange fluid channels and thus the pump head to come in contact with a patient's blood, no cross-contamination will occur between patients because all those elements are disposable. The pump drive, the electronic control mechanisms, the TE cooler, and the manual input unit, however, are all reusable for economy and convenience. Likewise, the sensors may be disposable, but the control unit to which they attach is reusable.

It will readily be appreciated by those of skill in the art that the system described here in detail may be employed using numerous substitutions, deletions and alternatives without deviating from the spirit of the invention as herein claimed. For example, but not by way of limitation, the serpentine pathway may be a coil or other suitable configuration, the sensors may sense a wide variety of body locations and other parameters may be provided to the control unit, such as temperature or pressure, the heat exchanger may be any appropriate type, such as a thermal electric heating unit which would not require the circulation of heat exchange fluid. If a heat exchange balloon is provided, a pump might be provided that is a screw pump, a gear pump diaphragm pump, a peristaltic roller pump, or any other suitable means for pumping the heat exchange fluid. All of these and other substitutions obvious to those of skill in the art are contemplated by this invention.

FIGS. 17A-E provide illustrations an embodiment of a heat exchanger of the invention. As shown in FIG. 17A, a heat exchange balloon catheter 360 with a finned balloon portion 362 may be positioned within at least a portion of the descending aorta 364 and a blood vessel 366 conducting blood flow to the brain region. It should be understood that the balloon portion 362 may be formed of material that is sufficiently thin to promote effective thermal transfer between heat exchange fluid within the balloon and blood flowing within heat exchange proximity of the balloon, but not excessively elastic to expand and unintentionally obstruct a fluid passageway or blood vessel 366. Indeed, the use of thin, strong but relatively inelastic material such as PET is desirable to obtain a predictable balloon configuration with adequate heat exchange properties. The catheter shaft 368 of the thermal catheter 360 provided herein may be placed in a desired location relative to a selected body region or artery 366 by conventional techniques such as guiding catheters or steerable wire over-the-wire technique as known to those of ordinary skill in the field. The balloon portion 362 of the catheter 360 may support the closed-loop circulation of a heat transfer fluid as described herein. The increased surface area may provide effective heat transfer within a body region by thermal conduction, and may further permit blood continued blood flow without substantial disruption by creating channels exterior of the balloon surface when the balloon is expanded.

FIG. 17B illustrates a heat exchange balloon 360 mounted on a shaft 368 defined by a longitudinal axis and a plurality of heat transfer fins 369, 371, 373, 375 projecting radially outward from the longitudinal axis 370 of the catheter shaft. The heat transfer fins may be formed, for example, as the lobes of a multi-lobed, collapsible balloon. The shaft 368 is generally round and in this embodiment includes a working lumen 370 running through the shaft and open at the distal end of the catheter. The working lumen may be used for the injection of medicaments which may include, for example, a thrombolytic agent, an anticoagulant, a neuro-protectant, a barbiturate, a anti-seizure agent, an oxygenated perfusate, a vasodilator, an agent which prevents vaso-spasm, an agent to prevent platelet activation, and an agent to deter the adhesion of platelets. Alternatively, the working lumen may be used for the injection of flouroscopic dye, for the receipt of a guide wire 329, or as a guiding catheter for various diagnostic or therapeutic devices including, for example, an angioplasty catheter, an embolectomy catheter, an occlusion member delivering catheter, an embolization member delivering catheter, an electro-cautery device, or a microcatheter. The shaft exterior of the central lumen is divided by a web 372 into two channels, an inlet channel 374 and an outlet channel 376. The shaft has inlet orifices 377, 378, 379 communicating between the inlet channel and the interior of the balloon at the distal portion of the balloon. The shaft also has outlet orifices 380, 381, 382 communicating between the interior of the balloon and the outlet channel. A plug 384 is inserted in the outlet channel between the inlet and the outlet orifices. The web 372 may be removed from the shaft between the plug and the inlet orifices to reduce resistance to flow of the heat exchange fluid in this portion of the shaft. Alternatively, in an embodiment not illustrated here, a tube with an open round lumen may be spliced between the plug in the outlet channel and the inlet orifices to provide a channel under the balloon for relatively unobstructed flow of the heat exchange fluid.

The balloon may be made of, for example, a single sheet of collapsible thin plastic material 285 sufficiently thin to allow for effective thermal exchange between a heat exchange fluid on the interior of the balloon and blood flowing over the exterior of the balloon. Tacking the material to the shaft as shown at 286 may form lobes of the balloon. Tacking the sheet of plastic to itself in appropriate locations as shown at 287 and 288 may further shape the lobes. The lobed shape of the balloon surface provides for significant surface for heat exchange while providing for continued flow past the balloon through the space between the lobes of the balloon.

In use, heat exchange fluid (not shown) may be pumped under mild pressure into the inlet channel 374. The heat exchange fluid may be, for example, sterile saline or other biocompatible fluid with appropriate heat transfer characteristics. The heat exchange fluid flows down the inlet channel until it reaches the inlet orifices 377, 378, 379 at the distal end of the balloon. The fluid flows from the inlet channel into the interior of the balloon. It then flows in a proximal direction through the interior of the balloon until it reaches the outlet orifices 380, 381, 382 at the proximal end of the balloon. The heat exchange fluid then flows from the interior of the balloon through the outlet orifices and into the outlet channel 376 where it then flows back down the shaft and out of the body.

In the manner described above, a heat exchange fluid may be circulated through the balloon and either give off heat if the fluid is hotter than the blood flowing past the balloon, or absorb heat from the heat exchange fluid is cooler than the blood.

FIGS. 18A-E provide illustrations of another variation of the invention heat exchange catheter 390 formed with a sleeve having an inner fluid passageway 392 that provides regionally confined thermal transfer. The heat transfer catheter 390 may comprise a blood channeling sleeve 394 for placement within a fluid-containing body region, the sleeve defined by a proximal region 396 and a distal region 398 formed with an inner fluid passageway 392 defined by at least one relatively proximal opening 395 and at least one relatively distal opening 399 each in communication with the fluid-containing body region for directing the flow of fluid within the catheter body 394. A heat exchanger is internally positioned within at least a portion the sleeve for regionally confined heat transfer with fluid within the inner fluid passageway 392 of the blood channeling sleeve. In FIGS. 18A-E the heat exchanger illustrated is a fluted closed-loop exchanger positioned around the circumference of the interior passageway 392 for circulation of heat exchange fluid as described in greater detail below.

Figure 18A:
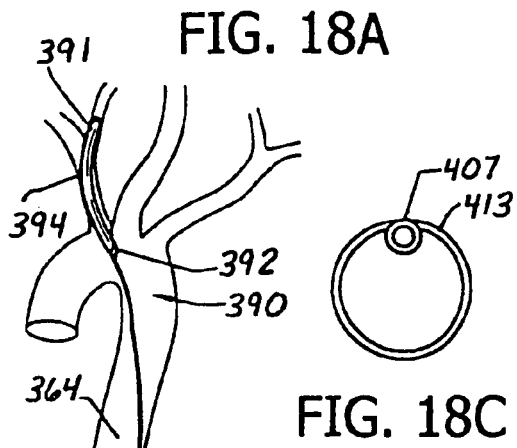
FIG. 18A is a simplified perspective view of a variation of the heat transfer catheter of the invention in place within the aorta, the innominate artery, and the right common carotid artery.
Figure 18B:
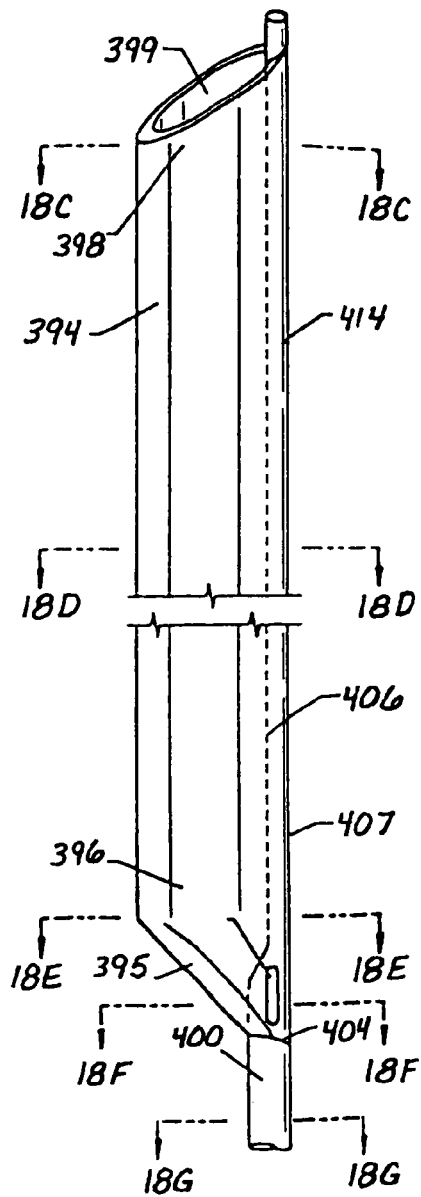
FIG. 18B is a perspective view in greater detail of the heat transfer catheter of FIG. 18A formed with a blood channeling sleeve defined by openings that may be in communication with a fluid-containing body region.
Figure 18D:
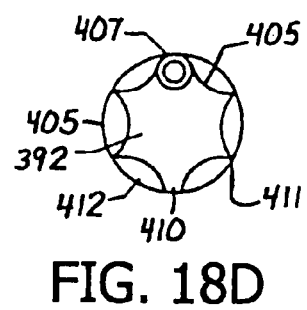
FIG. 18D is a simplified cross-sectional view of the catheter illustrated in FIG. 18B taken along line D-D.
Figure 18E:
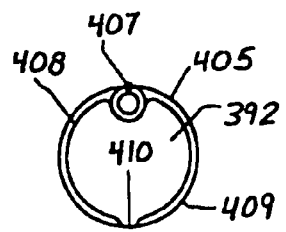
FIG. 18E is a simplified cross-sectional view of the catheter illustrated in FIG. 18B taken along line E-E.
Figure 18F:
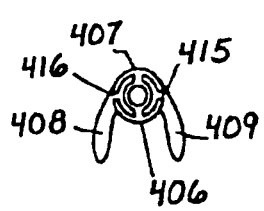
FIG. 18F is a simplified cross-sectional view of the catheter illustrated in FIG. 18B taken along line F-F.
Figure 18G:
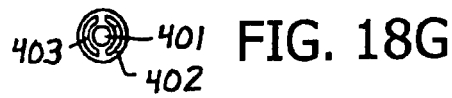
FIG. 18G is a simplified cross-sectional view of the catheter illustrated in FIG. 18B taken along line G-G.

As shown in FIG. 18A, the temperature regulating catheter 390 may be positioned within at least a portion of the aorta 364 and a blood vessel 399 branching off the aorta to direct blood to the brain region. The catheter is positioned in the innominate artery, but could equally be positioned, for example, with its distal portion in the right common carotid artery, the left common carotid, the right internal carotid and the left internal carotid among other locations. Blood may therefore be directed into the brain region while passing the heat exchanger positioned within the inner fluid passageway 392 of the catheter body 394. When the heat exchanger is configured for cooling blood flowing through the inner passageway 392 and the catheter is positioned as shown in FIG. 24A, localized hypothermia of the brain region may be effectively achieved. The temperature regulating catheter 390 may be also selected for applicable methods for controlling the temperature of other selected fluid-containing body regions, for example, where the catheter is positioned to selectively direct blood to those regions.

As illustrated in greater detail in FIGS. 18 B-G, the catheter may be formed with a proximal shaft 400, the proximal shaft having a central working lumen and two arc-shaped lumens in side-by side configuration. The two lumens comprise an inlet lumen 402 and an outlet lumen 403. The blood channeling sleeve is attached to the proximal shaft at a proximal attachment region 404. The sleeve comprises a layer 405 of very thin material such as a PET sheet formed into a large tube-like configuration. The catheter shaft is positioned down the inside of the tube, and the sheet is attached along both the top 406 and the bottom 407 of the catheter shaft along the length of the sleeve. This creates two wing-like channels 408, 409 on each side of the catheter running the length of the sleeve that are the inlet and outlet channels respectively. The outer layer of the plastic sheet of each of these channels may be connected together at the top of the channels 410 to form the tube-like structure that forms the sleeve. In addition, the two layers of plastic sheet that form each channel may be connected together at various points or along lines 411 along the length of the sleeve to form pleats 412, and the inner layer 405 may be loose so that the channels will billow when inflated.

At the proximal end of the sleeve, just distal of the attachment region 404, an orifice 415 is formed between the inlet lumen 402 and the inlet channel of the catheter shaft 409, and similarly an orifice 416 is formed between the outlet lumen 403 and the outlet channel 408 of the sleeve. At the distal portion of the sleeve, the inlet 409 and outlet 408 channels between the plastic sheets are connected, so that there is a common space 413 shared by the two channels to allow fluid flowing down the inlet side to be removed through the outlet side as described in greater detail below. The catheter shaft under the sleeve may have reduced profile as illustrated in FIG. 18 B so that the sleeve formed of the thin plastic sheets may be folded down onto the catheter shaft and have a suitably low profile.

As an alternative method of construction, two tubes may be used to create the sleeve. The catheter shaft is inserted into a large outer tube, and a slightly smaller inner tube is inserted into the outer tube but over the catheter shaft. The outer tube is sealed along its length on the bottom of the catheter shaft, and the inner tube is sealed along its length on the top of the catheter shaft. The inner and outer tubes are sealed to each a line opposite the catheter shaft to form two channels between them. The seal opposite the shaft does not extend all the way to the distal end which functions to create the common space for communication between the inlet and outlet channels.

Yet another method of constructing such a device is to invert a large tube of thin plastic to create an inner passageway bounded by two layers of thin plastic, with the thin plastic layers essentially attached at their distal end. The space between the two plastic layers forms the inlet and outlet channels. The catheter shaft may be placed within the inner passageway, and the two layers sealed to each other and to the catheter shaft along the bottom of the catheter shaft for the length of the inner passageway. The two layers of plastic are also sealed to each other along the top of the inner passageway from the proximal opening to a point just short of the distal end of the passageway. This creates an inlet channel 409 and an outlet channel 408 while leaving a common space 413 at the distal end of the sleeve.

In use, heat exchange fluid (not illustrated) is introduced under pressure into the inlet lumen 402 of the proximal shaft 404. It is directed down the shaft to the inlet orifice 415, at which point it enters the inlet channel 409 between the two layers of the plastic sheet on the inlet side. The fluid is then directed down the inlet channel, essentially inflating the billowing pleats of the sleeve somewhat. The fluid enters the common space 413 at the distal end of the blood channeling sleeve, and thereby enters the outlet channel 408 formed between the layers of plastic sheet on the outlet side of the sleeve. The fluid travels back down the length of the sleeve through the pleated channel to the outlet orifice 416 formed between the outlet channel 408 and the outlet lumen 403 in the catheter shaft. The fluid then travels down the outlet channel and out of the body. In this way, heat exchange fluid may be circulated through the structure to create heat exchange between blood flowing through the inner passageway in heat exchange proximity with the heat exchange fluid.

The formation of the inner passageway using a thin plastic sheets allows blood channeling sleeve to be collapsed to a low profile, for example, wrapping or folding it onto the reduced profile portion of the catheter shaft. This in turn provides a low profile device for insertion into the vascular system. When inflated by circulating heat exchange fluid, the billows created by the pleating of the plastic sheet increases the surface area for heat exchange between the heat exchange fluid flowing in the catheter body and blood or other body fluid in heat exchange proximity within the interior passageway.

Figure 19:
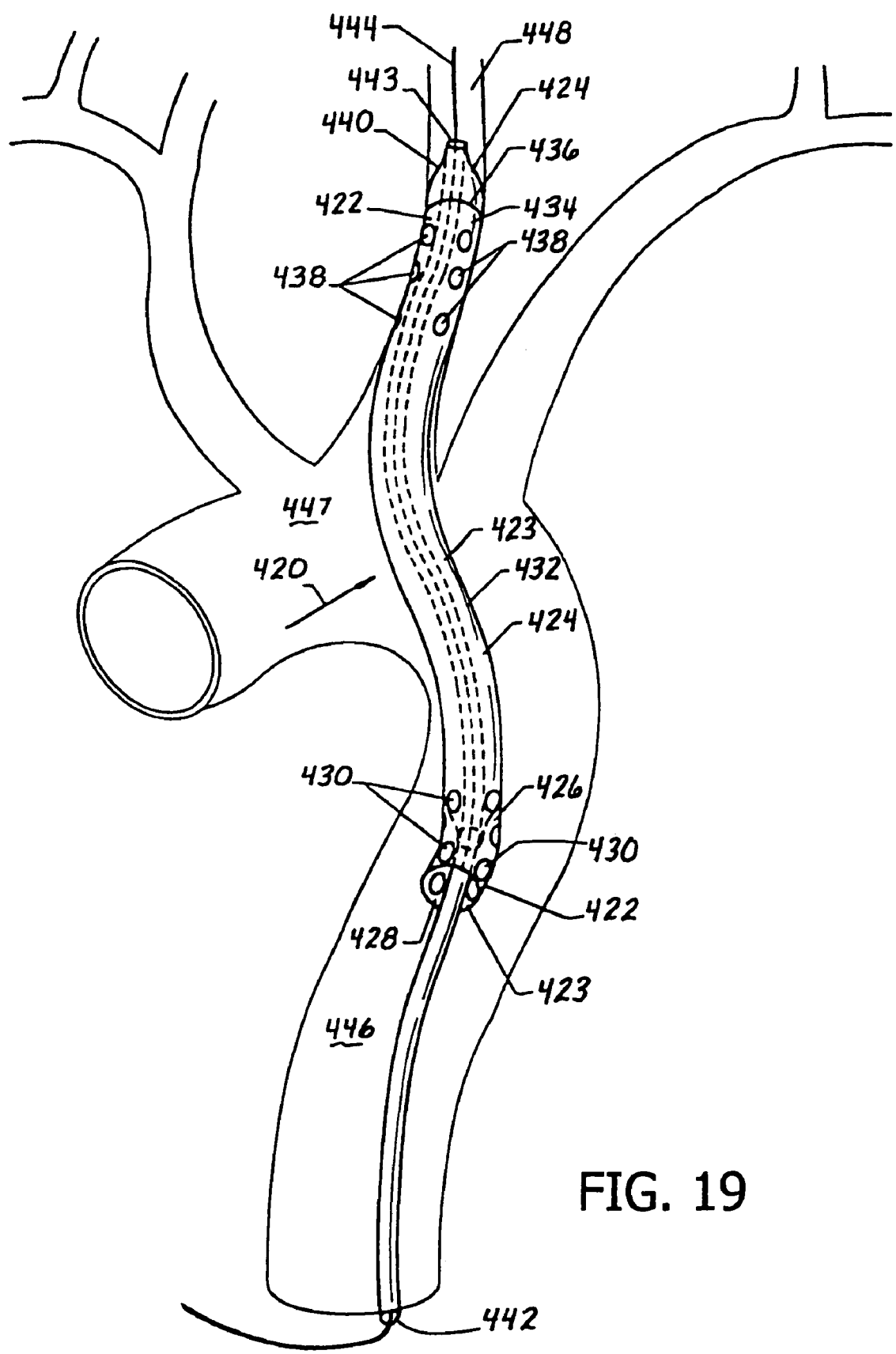
FIG. 19 is a simplified illustration of a heat transfer catheter shown in the aorta and having a blood channeling sleeve with a proximal opening in the descending aorta and a distal opening in the left common carotid artery.

In another embodiment, as illustrated in FIG. 19, a heat transfer catheter 420 may have a catheter body 422 formed as a blood channeling sleeve forming an inner passageway 423 with a heat exchanger such as a heat exchange balloon catheter 424 positioned within the inner passageway 423. The heat exchanger may be any suitable heat exchanger, but in the embodiment shown the heat exchanger is a heat transfer balloon catheter, for example the type described in the previous sections or depicted in FIG. 17B or FIG. 24A below. The heat exchanger should be suitably sized and configured to provide sufficient heat exchange capabilities but allow adequate flow of fluid through the inner passageway.

The blood channeling sleeve has a proximal section 426 having a proximal opening 428. The wall of the sleeve in the proximal section may additionally form orifices 430 to further enhance perfusion of fluid from the surrounding body portion into the inner passageway.

The sleeve further has an intermediate section 432. The wall of the sleeve in the intermediate section is generally solid so that it generally will not permit fluid to exit the inner passageway through the wall of the sleeve in the intermediate section. The wall of the sleeve in the intermediate and indeed throughout its length, may be formed of a material with thermal insulation properties to thermally insulate fluid within the inner passageway from the tissue such as blood outside of the inner passageway. Thus fluid entering the inner passageway at the proximal section will be channeled through the intermediate section to the distal section 434 of the blood channeling sleeve.

The distal section 434 of the blood channeling sleeve has a distal opening 436. Further, the wall of the blood channeling sleeve at the distal section may form orifices 438 that further enhance the flow of fluid out of the inner passageway and into the surrounding body portion such as a blood vessel. The distal end of the sleeve 436 may be proximal of the distal end of the heat exchanger 440, may be co-extensive with the end of the heat exchanger (not shown) or may extend distal of the heat exchanger as is shown in FIG. 26.

Additionally, there may be a central working lumen 442 that extends from the proximal end of the catheter shaft outside the patient's body to the distal end of the catheter shaft 443. The central lumen may extend past the distal end of the heat exchange balloon or even past the distal end of the sleeve. The working lumen may be used to accommodate a guide wire or to inject dye or insert a microcatheter for additional procedures such as lysing a clot or performing injections through the microcatheter or any of the other uses for the working lumen as described above, particularly in reference to the working lumen shown in FIG. 17. It will readily be appreciated that any of the above uses of the working lumen may be performed before, after, or even during the cooling of blood within the blood channeling sleeve. It may be one advantage of a catheter of the invention having a working lumen that the working lumen may be used for any of the above purposes at the same time that cooling is taking place and without inhibiting the cooling function of the catheter.

In use, the heat transfer catheter is placed in a fluid containing body, for example, as illustrated in FIG. 19, the arterial system. The proximal end of the blood channeling sleeve may be, for example, located in the descending aorta 446. The distal end of the catheter body is positioned as desired, in the case illustrated, in the left common carotid artery 448, which delivers blood to the brain. The pressure differential between the aorta at the level of the proximal end of the sleeve and the left common carotid artery at the distal end of sleeve is sufficient to cause blood to flow through the sleeve, into left common carotid artery and thence to the brain. In the case illustrated, blood enters the inner passageway of the blood channeling sleeve located in the aorta, and travels through the inner passageway and in heat exchange proximity with the heat transfer balloon 424 in which heated or cooled heat exchange fluid is circulating. The blood is thus heated or cooled. The heated or cooled blood is then channeled out the distal end of the inner passageway where it flows into the left common carotid artery. If the heat exchanger is cooling the blood, cooled blood would thus be directed into the left common carotid and bath the brain in cooled blood. This, in turn, if maintained for a sufficient length of time, may result in regional cooling of the brain tissue with the advantages of that condition noted above.

It should be noted that the placement of the proximal opening of the blood channeling sleeve 423 down the descending aorta some distance from the aortic arch 447 will provide for a longer path for the blood to travel over the heat exchange balloon catheter in reaching the right common carotid than would be the case if blood were captured and directed through the inner passageway by a blood-channeling sleeve located entirely within the left common carotid artery. This longer flow path provides for increased cooling effect relative to the shorter path. Also, the placement of the blood channeling sleeve at least partially in the aorta provides for the use of a larger heat exchanger, for example a heat exchange balloon of greater diameter, than would be possible if the heat exchange portion of the catheter body was located in the right common carotid artery since the aorta is significantly larger in diameter than the right common carotid artery.

The distal section 434 of the blood channeling sleeve may also form a relatively tight fit around the blood vessel in which it is located. In this way, the pressure differential between the proximal and distal end of the sleeve is maximized, and essentially all the blood flowing from, for example, the aorta to the carotid artery passes through the inner passageway and is heated or cooled by the heat exchanger. The wall of the blood channeling sleeve may form an occlusive shoulder to facilitate the sealing of the artery. The heat exchanger is, for example, a heat transfer balloon that holds the walls of the catheter body extended, and the heat exchange balloon has fins or the like that will permit significant blood flow between the heat exchange balloon fins and between the inner walls of the inner passageway and the balloon, most if not all the blood entering the right common carotid artery would pass over the heat exchanger and thus is treated by heating or cooling.

Figure 20:
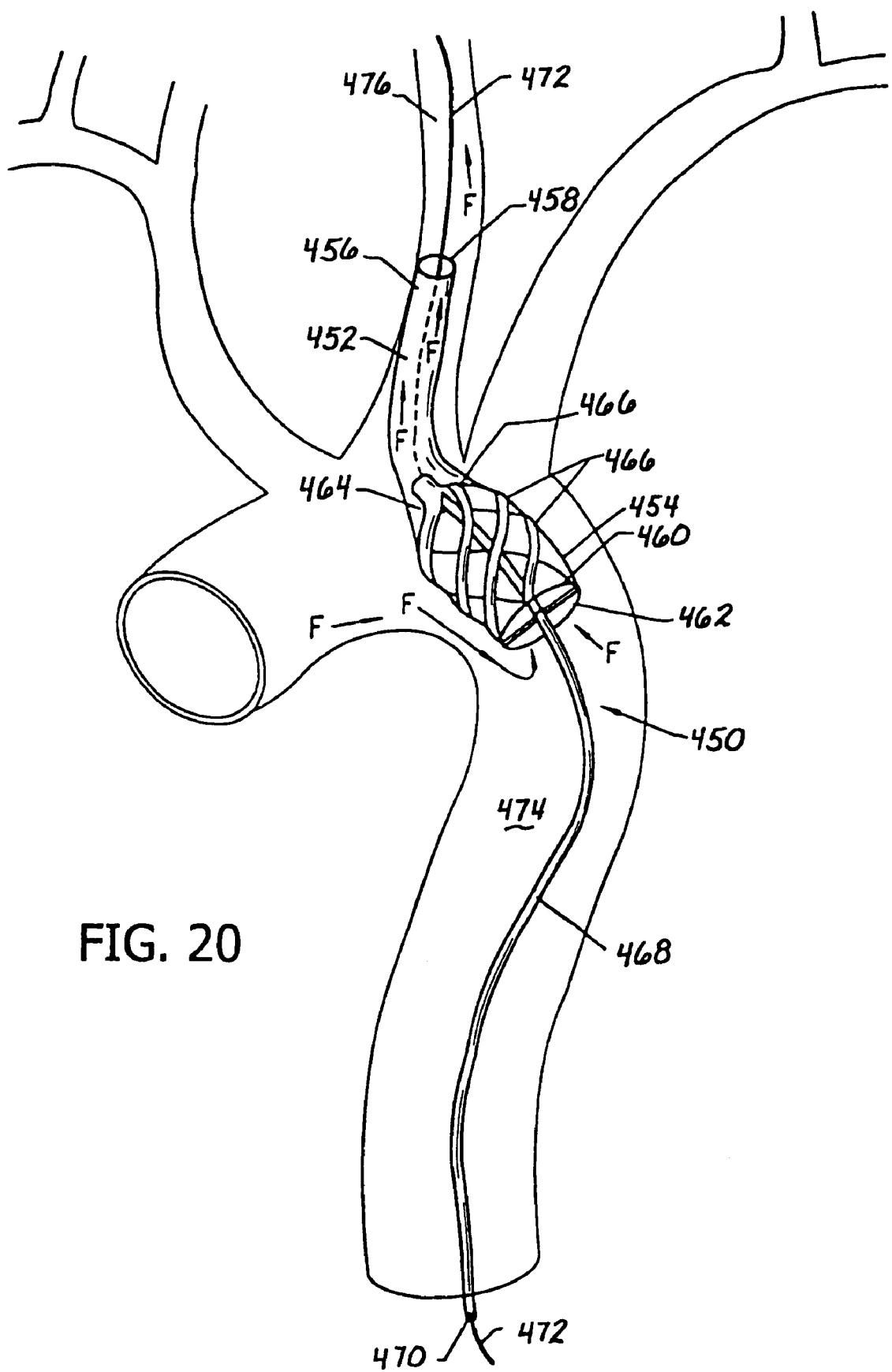
FIG. 20 is a simplified perspective view of a variation of the heat transfer catheter of the invention formed with an elongated shaft and a tapered catheter body with spiral shaped fins, and located in the aorta and left common carotid artery.

Another embodiment of the heat transfer catheter of the invention is illustrated in FIG. 20. The catheter 450 may be provided with a blood channeling sleeve 452 for the receipt and direction of body fluid such as blood. The sleeve may be essentially funnel shaped, having a distal region 454 that is significantly larger in diameter than its distal region 456. In this manner, the exterior surface of the blood channeling sleeve may form an occlusive shoulder that may be pressed or rest against appropriate anatomical structures such as the interior of the artery in question, so that most or virtually all of the blood entering the artery in question is directed through the interior passageway 464 of the blood channeling sleeve before entering the artery. In the example illustrated, the artery into which the catheter body is inserted is the left common carotid artery, but it may be readily appreciated by those of skill in the art that the distal portion of the blood channeling sleeve may be configured for similar placement in other desired locations.

The distal region may be elongate with a substantially cylindrical shape and terminate in a distal opening 458. Likewise, the proximal region may have a proximal opening 460 which may have a valve 462 for opening or closing the proximal opening or otherwise controlling entrance of the blood to the interior passageway 464 within the catheter body.

The interior of the proximal region 454 contains a heat exchanger. The heat exchanger depicted is a series of spiral fins 466 which may contain contains heat transfer balloons or balloon lobes for circulating heat transfer fluid. Alternatively the fins may be other types of heating or cooling mechanisms such as electric resistance heaters.

The heat transfer catheter may be provided with a catheter shaft 468 which may be provided with a working lumen 470 which may extend out of the patient's body when the heat exchange catheter is in place, and thus provide for the injection of drugs, fluoroscopic dye, or the like, and may accommodate a guide wire 472 for the placement of the heat transfer catheter. The shaft may also have channels (not shown) for the flow of heat transfer fluid, or contain electrical wires (not shown) to connect to the heat exchangers or sensors (also not shown) on the catheter.

In use, the heat transfer catheter 450 is placed in the desired body location. In the illustration of FIG. 20 the catheter is placed so that the proximal portion of the blood channeling sleeve 454 is within the aorta 474 and the distal portion 456 is within the left common carotid artery 476. Blood flows down the aorta (illustrated with the arrows labeled "F") and may enter the proximal opening 460 of the catheter body if the valve 462 is open. The pressure differential between the blood in the aorta and the blood in the left common carotid is sufficient to cause the blood to flow up the inner passageway. As the blood flows up the inner passageway it passes in heat exchange proximity with the heat exchange fins 466 and is heated or cooled. The heated or cooled blood is channeled into the left common carotid by the blood channeling sleeve, and ultimately the heated or cooled blood baths the brain. If maintained for a sufficient length of time this may result in regionally heating or cooling of the brain.

Another embodiment of the heat transfer catheter of the invention is illustrated in FIG. 21. The catheter 490 illustrated in that drawing is provided with a blood channeling sleeve 492 that is configured for placement in the blood vessels of the patient's body, for example the main arteries leading to the brain region 494. The blood channeling sleeve is essentially cylindrical in shape, but may have a slightly enlarged proximal section 496 that creates a shoulder in the catheter body that may act as an occlusive shoulder 498 when the blood channeling sleeve is placed in an artery, such as an artery branching off the coronary arch.

The blood channeling sleeve is shaped as a tube and forms an inner passageway 500 that extends from the proximal section 496 that begins with a proximal opening 502 to the distal end which terminates at a distal opening. 504. A heat exchanger such as a fined balloon heat exchange catheter 506 as described and illustrated in FIGS. 17 B and 24 A is located in the catheter body and may be contained entirely within the inner passageway 500 of the sleeve. The fins 508 provide for added heat transfer surface relative to a cylindrically shaped heat exchange balloon, and also create flow channels between the fins for the flow of blood from the proximal opening, over and between the fins of the heat exchange balloon, and out the distal end of the inner passageway. A catheter shaft 509 may also be provided as described in conjunction with the other embodiments described above.

FIGS. 21B-D illustrate the operation of a control system to regulate the opening and closing of a valve assembly 460 that may be formed along any section of the sleeve 492 such as at the proximal opening 502 in order to control the flow of blood within the inner passageway 500. For example, a bi-leaflet valve 510 may be positioned at the proximal opening of the sleeve 492 around the catheter shaft. The valve 510 may have at least one closed position as shown in FIG. 21B and at least one open position as shown in FIG. 21C. Other valves such as one-way valves may be selected for the catheter body, and the valve may be opened and closed to a variable degree to control the amount of fluid passing through the sleeve at selected points in time.

The valve 510 may be synchronously opened and/or closed in accordance with the heartbeat of a patient as illustrated by the graph of FIG. 21D. Because aortic blood flow (L/min) is pulsatile and fluctuates at different time intervals during the heartbeat cycle, a valve may be selectively opened when a relatively large amount of blood is released from the heart. At the same time, the valve may be selectively closed to retain the blood within the inner passageway 500 when the blood flow is slower. Alternatively, the valves may be controlled to cause blood to flow more slowly through the inner passageway to allow for all the blood passing in to the artery distal of the catheter body flows slowly over the head exchanger for maximum heating or cooling.

As described above, a catheter control unit may simultaneously monitor body conditions or sensed stimuli such as the heart rate, temperature at various locations, and pressure within the apparatus or within the patient. When the valve 510 is in a closed position (FIG. 21B), blood or fluid is retained within the inner passageway 500 and effectively cooled by the internally positioned heat exchanger 506. A valve in a closed position may prevent or minimize backflow of cooled fluid away from the brain. After the blood is allowed to cool, when the heart begins to send more blood in the direction of the heat transfer catheter, the valve may be activated to assume an open position (FIG. 21C) to allow the cooled blood to be pushed out of the confined cooling area by the relatively warmer incoming blood. When the pressure or surge of blood from the heart subsides thereafter, the valve 510 may again close, and this cooling and pumping cycle continues repeatedly until the desired level of regional hypothermia in the brain is achieved. FIG. 21D is a graphic representation of the cycle just described.

Figure 22:
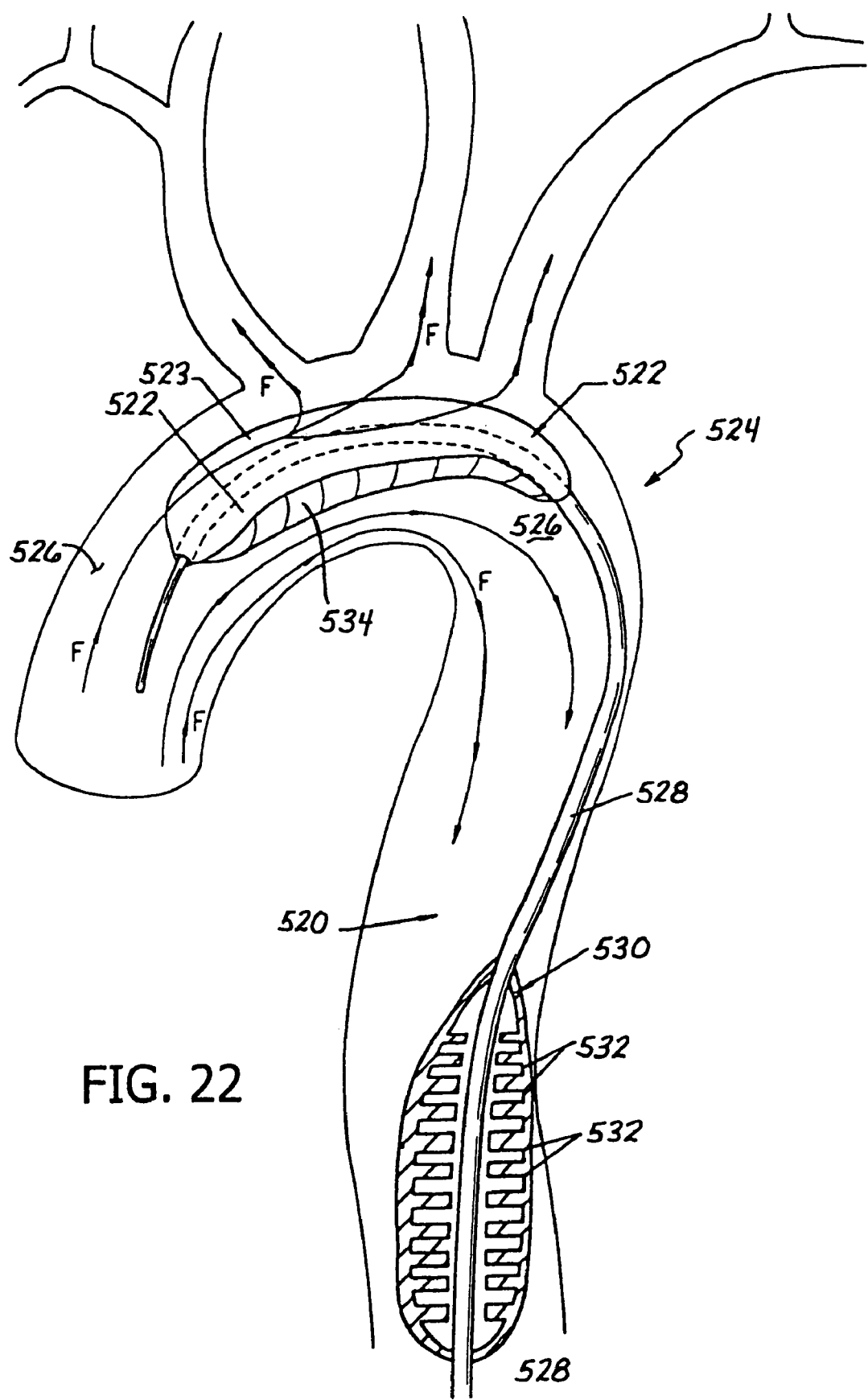
FIG. 22 is a heat transfer catheter with a plurality of heat transfer regions that may be configured for placement in the aortic region.

Although many of the embodiments of the invention described thus far are illustrated as either a cooling apparatus or a heating apparatus, it should be understood that any combination of these variations may form a series or a network of thermoregulating devices. For example, as shown in FIG. 22, a heat exchange catheter 520 includes a heat transfer balloon 524 with a plurality of collapsible cooling fins 522 placed in the aortic 526 region. A suitable heat transfer balloon catheter with fins has been previously described. The heat exchange catheter may be provided with a catheter shaft 528. The heat exchange catheter may have a heating element 530 formed at a different location along the catheter shaft than the cooling balloon 524. The shaft 528 may include a pair of longitudinal fluid paths (not shown) for circulating hot heat transfer medium to the heating element as well as an additional pair of fluid paths (not shown) that circulate cold heat transfer medium to the cooling balloon 522. Alternatively, the heating fin 530 may include a resistance heater or other heating elements known in the art. In the case of a resistance heating element, electrical current may pass through wires within the shaft (not shown) to the heat-generating element.

The cooling balloon 522 may include an insulated underside 534. Blood flowing in a certain direction, for example to the brain region, may thus be preferentially cooled relative to blood flowing to other areas of the patient's body, for example to the lower body. In the example illustrated in FIG. 22, the heat transfer region includes a curved cooling balloon that is thermally insulated along the inner radius of its curvature and thermally conductive along its outer radius of its curvature. The cooling balloon may be placed in the aortic arch. Blood is pumped by the heart into the aorta (indicated by arrows F) and some flows over the top surface 523 of the cooling balloon 522 in heat exchange proximity to the balloon surface. This blood is cooled, and the cool blood then flows naturally to the brain region. Blood flowing past the inner, insulated curvature of radius 525 is not cooled, and thus blood of normal temperature flows down the aorta and to the lower body. It may be noted that, in the example illustrated, cool blood flows to the brain region through all of the arteries extending from the aortic arch without the need to cannulate each of those arteries. In such a configuration, it is also unnecessary to provide the heat transfer catheter with a blood channeling sleeve since the directional cooling is obtained without using the catheter to direct the cool blood to specific arteries.

As described, heating and cooling mechanisms may be formed at various locations along the shaft 528 of the heat transfer catheter 524. Alternatively, multiple heating and cooling catheters may be used in combination or cooperatively. As previously described, a common catheter control unit may monitor and control multiple devices individually or collectively, and may be responsive to one or more sensors (not shown) such as pressure sensors or temperature sensors.

Figures 23A, 23B:
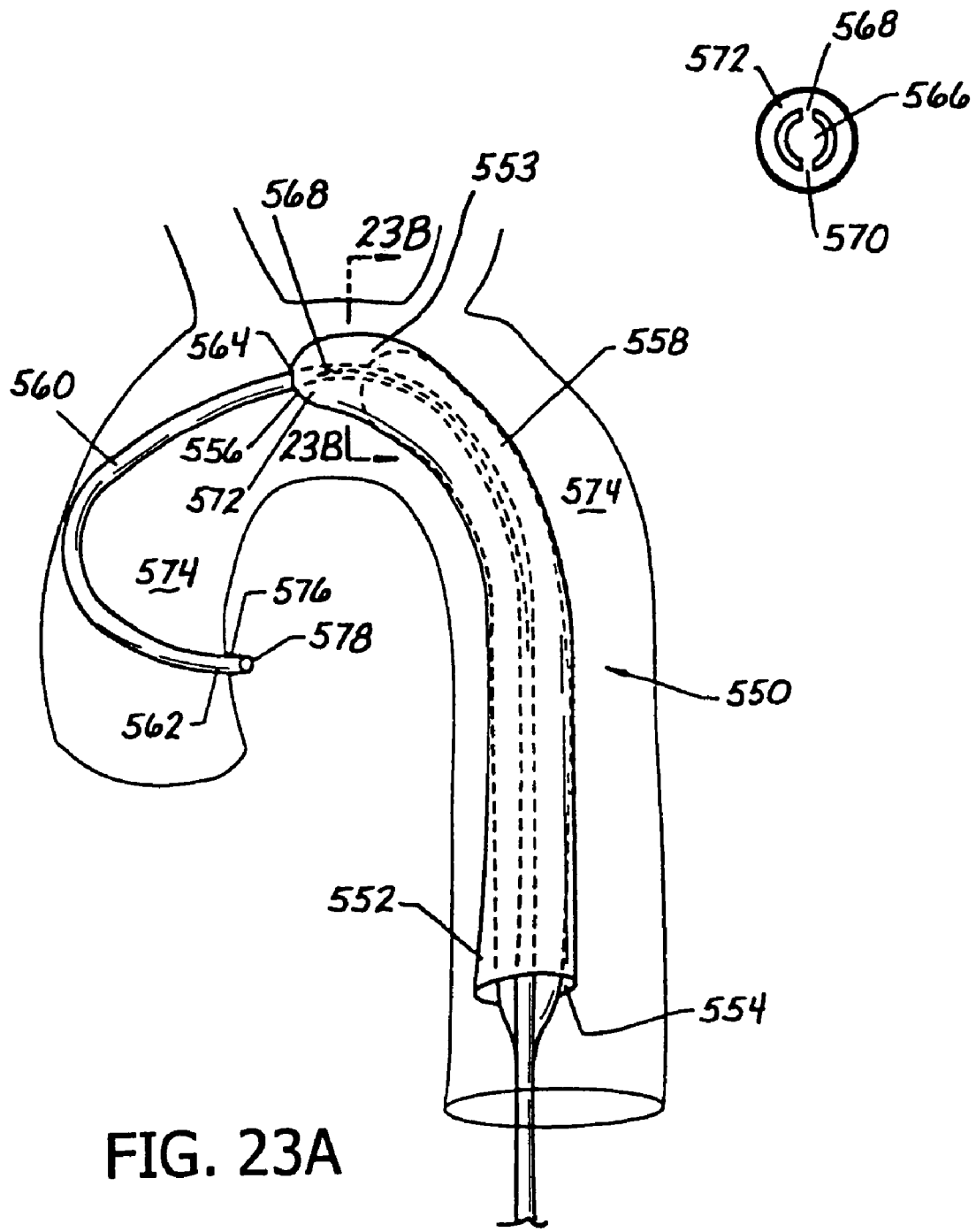
FIG. 23A is a simplified perspective drawing of a version of the heat exchange catheter of the invention having an entry for cooled blood into a central lumen, the distal end of the central lumen inserted into the coronary ostium.
FIG. 23B is a cross-sectional view of FIG. 29 taken along lines B-B.

Another aspect of the invention is illustrated in FIG. 23 whereby heated or cooled blood may be directed to a specific location such as a tumor, or organ such as the heart, through a relatively small vessel. A heat transfer catheter 550 is provided having a blood channeling sleeve 552, which sleeve has a proximal opening 554 and a distal end section 552. A heat exchanger 558 which may be, for example, a finned heat transfer balloon as described above, is located within the blood channeling sleeve. The heat transfer catheter has a catheter shaft 560, which extends from at least the interior of the blood channeling sleeve to a distal end 562. The distal section of the sleeve is sealed around the catheter shaft 564. The catheter shaft 560 has a perfusion lumen 566 extending between blood inlet orifices 568, 570 formed in the catheter shaft at a point within the blood channeling above, and the distal end 562 of the shaft. The blood inlet orifices provide fluid communication between the perfusion lumen and the interior 572 of the blood channeling sleeve.

In use, the heat transfer catheter 560 is placed into a patient's vasculature, for example the aorta 574, and is positioned so that the distal end 562 of the catheter shaft 560 in a desired location, for example, in the coronary ostium. The pressure differential between the blood in the aorta at the proximal end of the blood channeling sleeve 552 and the distal end 566 of the catheter shaft causes blood to flow through the proximal opening of the sleeve, through 554 the inner passageway and in heat transfer proximity to the heat exchanger at which time the blood will be heated or cooled, and into the blood inlet orifices through the central lumen of the catheter shaft and out the distal tip of the central lumen 578. In this way, a stream of heated or cooled blood may be directed to a specific organ or tissue, for example the heart or tumor, and bath that organ or tissue in the heated or cooled blood. If a sufficient portion of the organ or tissue's blood supply is treated in this manner for a sufficient time, regional heating or cooling of the organ or tissue in question will result.

The central lumen may extend from the distal tip 578 to a proximal opening outside the body. In this way the central lumen may function as a working lumen for all applications as previously described including angiography and acting as a guide catheter for angioplasty. The central or working lumen may be sized to function as a guide catheter and allow simultaneous insertion of an angioplasty catheter and infusion of cold blood through the central or working lumen.

An alternative construction to the heat exchange balloon as illustrated in FIG. 17 is shown in FIG. 24A wherein the heat exchange region is formed using a series of three collapsible balloon lobes 902, 904, 906 located around a central collapsible lumen 908. A proximal shaft 910 is formed having two channels, an inlet channel 912 and an outlet channel 914. The interior of the shaft is divided into two lumens by webs 916, 917, but the lumens do not occupy equal portions of the interior of the shaft. The inlet channel occupies about ⅓ of the circumference of the interior, the outlet channel occupies about ⅔ of the circumference of the interior for reasons that will be explained below.

At the heat exchange region of the catheter, a transition 915 is formed between the shaft 910 and the tube 911 forming the central collapsible lumen 908. The outlet channel is plugged 917, the tube 911 is affixed over the shaft 910 by, for example gluing, at the transition 915, and the shaft ends with the tube (not shown). In this way, as shown in FIG. 24C, the inlet channel in this portion of the catheter occupies the entire circumference of the shaft. At the distal end of the balloon, inlet orifices 918, 920, 922 are formed between the inlet channel and the three collapsible balloons. At the proximal end of the heat exchange region, outlet orifices 924, 926, 928 are formed between the interior of each balloon and the outlet channel in the shaft. As may be seen in FIG. 30D, the configuration of the outlet channel is such that communication with the interior of each of the three balloons is possible.

As may be appreciated, heat exchange fluid (not shown) may flow down the inlet channel in the shaft 912, continue down lumen 908 to the distal end of the heat exchange region, exit the lumen through the inlet orifices 918, 919, 920 to the interior lumens of the balloon lobes 919, 921, 923, travel back down each of the three balloons and re-enter the shaft through the outlet orifices 924, 926, 928 and then down the outlet channel 914 toward the proximal end of the catheter. In this way heat exchange fluid may be circulated through the three balloons to add heat to the blood flowing in heat transfer proximity to the balloons if the heat exchange fluid is warmer than the blood, or to remove heat from the blood if the heat exchange fluid is cooler than the blood. The material from which the balloons are made is made of a material that will permit significant thermal exchange between the heat exchange fluid on the interior of the balloon and the body fluid such as blood flowing in heat exchange proximity to the surface of the balloon. One such appropriate material is very thin plastic material, which may also be made strong enough to withstand the pressure necessary for adequate flow of the heat exchange fluid.

It may also readily be appreciated that the same heat exchange balloon of the type described here and in conjunction with FIG. 17 may be used to add heat to the blood stream or remove heat from the blood stream depending on the relative temperature of the heat exchange fluid and the blood flowing in heat exchange proximity to the balloon. That is, the same device at the same location may be used alternately to add or to remove heat merely by controlling the temperature of the heat exchange fluid within the device.

A heat exchange device may also be supplied as a kit comprising the heat exchange device and a set of instruction for using the heat exchange device. The heat exchange device may comprise, for example, a heat exchange catheter as described in this application. The instructions for use will generally instruct the user to insert the heat exchange device into a body fluid containing region and to establish the temperature of the heat exchange device to affect the temperature of the body fluid. The instructions for use may direct the user to heat or cool the body fluid to achieve any of the purposes described in this application.

While all aspects of the present invention have been described with reference to the aforementioned applications, this description of various embodiments and methods shall not be construed in a limiting sense. The aforementioned is presented for purposes of illustration and description. It shall be understood that all aspects of the invention are not limited to the specific depictions, configurations or relative proportions set forth herein which depend upon a variety of conditions and variables. The specification is not intended to be exhaustive or to limit the invention to the precise forms disclosed herein. Various modifications and insubstantial changes in form and detail of the particular embodiments of the disclosed invention, as well as other variations of the invention, will be apparent to a person skilled in the art upon reference to the present disclosure. It is therefore contemplated that the appended claims shall cover any such modifications or variations of the described embodiments as falling within the true spirit and scope of the invention.

What is claimed is:

1. A method for cooling neural tissue located within the body of a mammalian patient, said method comprising the steps of:
   A. selecting a portion of the body containing the tissue, which portion receives a flow of a body fluid.
   B. providing a heat exchange catheter device which comprises; i) an elongate, flexible catheter having a proximal end, a distal end, and an insertion portion for insertion into a patient's body ii) at least one fluid lumen through which a thermal exchange fluid may be circulated and iii) a heat exchanger located a first location on the catheter along a length of said insertion portion which is less than the entire length of said insertion portion, said heat exchanger being operative to exchange heat between body fluid which flows in heat exchange proximity to said heat exchanger and the thermal fluid which is circulated through said catheter;
   C. inserting the catheter into the fluid-containing body structure of the patient and positioning the catheter such that fluid flowing through the body structure will pass in heat exchange proximity to the heat exchanger before reaching the selected body portion;
   D. circulating a heat exchange fluid through the fluid lumen of the catheter device, such that body fluid will pass in heat exchange proximity to the heat exchanger, said heat exchange fluid being at a temperature other than the body fluid, whereby the temperature of the body fluid will be altered, and will subsequently flow to said neural tissue;
   E. maintaining the catheter in said position and with the heat transfer fluid at said temperature for a sufficient time to alter the temperature of the neural tissue; and
   F. maintaining the selected portion of the body in Sten A at a temperature different than that of the rest of the patient's body;
   wherein Step F comprises wrapping at least a portion of the patient's body below the head in warming blankets.

2. The method of claim 1 wherein the fluid containing body structure recited in Step C is a blood vessel and the body fluid recited in Step A is blood.

3. The method of claim 2 wherein the blood vessel is an artery.

4. The method of claim 2 wherein the blood vessel is a vein.

5. The method of claim 1 wherein the body portion in Step A is the brain.

6. The method of claim 1 wherein the catheter device provided in Step A further comprises iv) a blood channeling sleeve formed about a segment of said catheter whereon said heat exchanger is located such that a blood flow space exists between said catheter and said blood channeling sleeve, said blood channeling sleeve having a blood inlet located proximal to at least a portion of the heat exchanger and a blood outlet located distal to at least a portion of said heat exchanger, and wherein the catheter is positioned in Step B such that blood which exits the blood outlet will flow to a blood vessel which perfuses said neural tissue.

7. The method of claim 6 wherein the catheter is further positioned in Step B such that the blood outlet is within a first blood vessel which leads to said neural tissue and the blood inlet is within a second blood vessel, blood from the second blood vessel being thereby channeled through the blood channeling sleeve in heat exchanging proximity to the heat exchanger, and subsequently flowing into said first blood vessel to cool said neural tissue.

8. The method of claim 7 wherein the neural tissue is located in the brain and the first blood vessel is selected from the group consisting of:
   right common carotid artery;
   left common carotid artery;
   innominate artery;
   right internal carotid artery; and,
   left internal carotid artery.

9. The method of claim 8 wherein the second blood vessel is the aorta.

10. The method of claim 6 wherein the blood inlet of the blood channeling sleeve is located within the descending aorta.

11. The method of claim 7 wherein at least a portion of the blood channeling sleeve is located in said first blood vessel, and has an outer diameter that is approximately as large as the luminal diameter of the first blood vessel such that blood is substantially prevented from entering the first blood vessel other than through the blood flow space between the catheter and the blood channeling sleeve.

12. The method of claim 11 wherein the first blood vessel is a branch vessel which emanates from the arch of the aorta and the second blood vessel is the aorta.

13. The method of claim 7 wherein at least a portion of the blood channeling sleeve is located in said first blood vessel, said blood channeling sleeve having a shoulder between said blood inlet and said blood outlet, said shoulder sized to cause at least a partial occlusion between said first blood vessel and said second vessel to prevent blood flowing from said blood vessel to said first blood vessel other than through said blood channeling sleeve.

14. The method of claim 1 further comprising the steps of:
providing a second heat exchange catheter device which comprises; 1) an elongate, flexible catheter having a proximal end and a distal end, ii) a heat exchanger located at a first location on the catheter, said heat exchanger being operative to exchange heat between blood which flows in heat exchanging proximity to its heat exchanger and the heat exchanger;
inserting the second catheter into the patient's vasculature and positioning said second catheter at a second location such that blood which has cooled the neural tissue in Step C of the method will subsequently flow in heat exchange proximity to the heat exchanger of the second catheter; and,
using said second catheter to add heat to blood that flows in heat exchange proximity to the heat exchanger of the second catheter.

15. The method of claim 1 wherein the catheter device provided in Step A further comprises a working lumen and wherein the positioning of the catheter in Step B is accomplished by advancing the catheter over a previously inserted guide wire such that the guide wire extends through the working lumen of the catheter.

16. The method of claim 1 wherein the catheter device provided in Step A further comprises a working lumen and wherein the method further comprises the step of:
infusing a medicament through the working lumen of the catheter to deliver said medicament to the neural tissue.

17. The method of claim 16 wherein the medicament is selected from the group of medicaments consisting of:
a thrombolytic agent;
an anticoagulant;
a neuro-protectant;
a barbiturate;
a anti-seizure agent;
an oxygenated perfusate;
a vaso-dilator;
an agent which prevents vaso-spasm;
an agent which inhibits platelet activation; and,
an agent which deters the adhesion of platelets.

18. The method of claim 1 wherein the catheter device provided in Step A further comprises a working lumen and wherein the method further comprises the step of:
infusing a radiographic contrast agent through the working lumen of the catheter to permit imaging in the area of said neural tissue.

19. A method for cooling neural tissue located within the body of a mammalian patient, said method comprising the steps of:
A. selecting a portion of the body containing the tissue, which portion receives a flow of a body fluid.
B. providing a heat exchange catheter device which comprises; i) an elongate, flexible catheter having a proximal end, a distal end, and an insertion portion for insertion into a patient's body ii) at least one fluid lumen through which a thermal exchange fluid may be circulated and iii) a heat exchanger located a first location on the catheter along a length of said insertion portion which is less than the entire length of said insertion portion, said heat exchanger being operative to exchange heat between body fluid which flows in heat exchange proximity to said heat exchanger and the thermal fluid which is circulated through said catheter;
C. inserting the catheter into the fluid-containing body structure of the patient and positioning the catheter such that fluid flowing through the body structure will pass in heat exchange proximity to the heat exchanger before reaching the selected body portion;
D. circulating a heat exchange fluid through the fluid lumen of the catheter device, such that body fluid will pass in heat exchange proximity to the heat exchanger, said heat exchange fluid being at a temperature other than the body fluid, whereby the temperature of the body fluid will be altered, and will subsequently flow to said neural tissue;
E. maintaining the catheter in said position and with the heat transfer fluid at said temperature for a sufficient time to alter the temperature of the neural tissue;
wherein the catheter device provided in Step A further comprises iv) a blood channeling sleeve formed about a segment of said catheter whereon said heat exchanger is located such that a blood flow space exists between said catheter and said blood channeling sleeve, said blood channeling sleeve having a blood inlet located proximal to at least a portion of the heat exchanger and a blood outlet located distal to at least a portion of said beat exchanger, and wherein the catheter is positioned in Step B such that blood which exits the blood outlet will flow to a blood vessel which perfuses said neural tissue.

20. The method of claim 19 wherein the catheter is further positioned in Step B such that the blood outlet is within a first blood vessel which leads to said neural tissue and the blood inlet is within a second blood vessel, blood from the second blood vessel being thereby channeled through the blood channeling sleeve in heat exchanging proximity to the heat exchanger, and subsequently flowing into said first blood vessel to cool said neural tissue.

21. The method of claim 20 wherein the neural tissue is located in the brain and the first blood vessel is selected from the group consisting of:
right common carotid artery;
left common carotid artery;
innominate artery;
right internal carotid artery; and,
left internal carotid artery.

22. The method of claim 21 wherein the second blood vessel is the aorta.

23. The method of claim 22 wherein the blood inlet of the blood channeling sleeve is located within the descending aorta.

24. The method of claim 20 wherein at least a portion of the blood channeling sleeve is located in said first blood vessel, and has an outer diameter that is approximately as large as the luminal diameter of the first blood vessel such that blood is substantially prevented from entering the first blood vessel other than through the blood flow space between the catheter and the blood channeling sleeve.

25. The method of claim 24 wherein the first blood vessel is a branch vessel which emanates from the arch of the aorta and the second blood vessel is the aorta.

26. The method of claim 20 wherein at least a portion of the blood channeling sleeve is located in said first blood vessel, said blood channeling sleeve having a shoulder between said blood inlet and said blood outlet, said shoulder sized to cause at least a partial occlusion between said first blood vessel and said second blood vessel to prevent blood flowing from said second blood vessel to said first blood vessel other than through said blood channeling sleeve.

27. A method for cooling neural tissue located within the body of a mammalian patient, said method comprising the steps of:
- A. selecting a portion of the body containing the tissue, which portion receives a flow of a body fluid;
- B. providing a heat exchange catheter device which comprises; i) an elongate, flexible catheter having a proximal end, a distal end, and an insertion portion for insertion into a patient's body ii) at least one fluid lumen through which a thermal exchange fluid may be circulated and iii) a heat exchanger located a first location on the catheter along a length of said insertion portion which is less than the entire length of said insertion portion, said heat exchanger being operative to exchange heat between body fluid which flows in heat exchange proximity to said heat exchanger and the thermal fluid which is circulated through said catheter;
- C. inserting the catheter into the fluid-containing body structure of the patient and positioning the catheter such that fluid flowing through the body structure will pass in heat exchange proximity to the heat exchanger before reaching the selected body portion;
- D. circulating a heat exchange fluid through the fluid lumen of the catheter device, such that body fluid will pass in heat exchange proximity to the heat exchanger, said heat exchange fluid being at a temperature other than the body fluid, whereby the temperature of the body fluid will be altered, and will subsequently flow to said neural tissue;
- E. maintaining the catheter in said position and with the heat transfer fluid at said temperature for a sufficient time to alter the temperature of the neural tissue;
- F. providing a second heat exchange catheter device which comprises; 1) an elongate, flexible catheter having a proximal end and a distal end, ii) a heat exchanger located at a first location on the catheter, said heat exchanger being operative to exchange heat between blood which flows in heat exchanging proximity to its heat exchanger and the heat exchanger;
- G. inserting the second catheter into the patient's vasculature and positioning said second catheter at a second location such that blood which has cooled the neural tissue in Step C of the method will subsequently flow in heat exchange proximity to the heat exchanger of the second catheter; and,
- H using said second catheter to add heat to blood that flows in heat exchange proximity to the heat exchanger of the second catheter.

* * * * *